US00RE41376E

(19) United States
(12) Reissued Patent
Torch

(10) Patent Number: US RE41,376 E
(45) Date of Reissued Patent: Jun. 15, 2010

(54) SYSTEM AND METHOD FOR MONITORING EYE MOVEMENT

(76) Inventor: William C. Torch, 4100 Ramrod Cir., Reno, NV (US) 89509

(21) Appl. No.: 11/732,828
(22) Filed: Apr. 3, 2007

Related U.S. Patent Documents

Reissue of:
(64) Patent No.: 6,542,081
Issued: Apr. 1, 2003
Appl. No.: 09/740,738
Filed: Dec. 18, 2000

U.S. Applications:
(63) Continuation of application No. 11/097,942, filed on Apr. 1, 2005, now Pat. No. Re. 39,539, which is a continuation-in-part of application No. 09/104,258, filed on Jun. 24, 1998, now Pat. No. 6,163,281, which is a continuation-in-part of application No. 08/978,100, filed on Nov. 25, 1997, now Pat. No. 6,246,344, which is a continuation-in-part of application No. 08/699,670, filed on Aug. 19, 1996, now Pat. No. 5,748,113.

(51) Int. Cl.
*G08B 23/00* (2006.01)

(52) U.S. Cl. ..... 340/575; 340/573.1; 340/576; 382/117; 600/558

(58) Field of Classification Search ..... 340/573.1, 340/575, 576, 825.19, 539.1; 382/117, 118; 600/558; 351/210
See application file for complete search history.

(56) References Cited

U.S. PATENT DOCUMENTS

| | | | | |
|---|---|---|---|---|
| 3,689,135 A | * | 9/1972 | Young et al. | 351/246 |
| 3,798,599 A | | 3/1974 | Kafafian | |
| 3,863,243 A | * | 1/1975 | Skolnick et al. | 340/575 |
| 3,966,310 A | | 6/1976 | Larson | |
| 4,102,564 A | | 7/1978 | Michael | |

(Continued)

FOREIGN PATENT DOCUMENTS

| | | |
|---|---|---|
| EP | 0 679 984 | 4/1995 |
| EP | 0 984 347 | 8/1998 |
| JP | 2000137792 | 5/2000 |
| WO | 9849028 | 11/1998 |
| WO | 2006092022 | 9/2006 |

OTHER PUBLICATIONS

PCT International Search Report for PCT/US/2005/011104, Applicant: Dr. William Torch, Forms PCT/ISA/210 & 220, dated Mar. 21, 2006 (9 pages).

PCT Written Opinion of the International Search Authority for PCT/US2005/011104, Applicant: Dr. William C. Torch, Form PCT/ISA/237, dated Mar. 21, 2006 (11 pages).

Hewlett–Packard GmbH: "Helmet–Mounted Display for Data Recall and Direct Consultation During Surgical Operation," Jan. 1996, Research Disclosure, Mason Publications, Hampshire, GB.

*Primary Examiner*—Thomas J Mullen
(74) *Attorney, Agent, or Firm*—William A. English; Vista IP Law Group LLP

(57) ABSTRACT

Apparatus for monitoring movement of a person's eye, e.g., to monitor drowsiness. The system includes a frame that is worn on a person's head, an array of emitters on the frame for directing light towards the person's eye, and an array of sensors on the frame for detecting light from the array of emitters. The sensors detect light that is reflected off of respective portions of the eye or its eyelid, thereby producing output signals indicating when the respective portions of the eye is covered by the eyelid. The emitters project a reference frame towards the eye, and a camera on the frame monitors movement of the eye relative to the reference frame. This movement may be correlated with the signals from the array of sensors and/or with signals from other sensors on the frame to monitor the person's level of drowsiness.

39 Claims, 23 Drawing Sheets

U.S. PATENT DOCUMENTS 4,359,724 A 11/1982 Zimmerman et al.
4,815,839 A * 3/1989 Waldorf ..... 351/210
4,850,691 A 7/1989 Gardner et al.
4,852,988 A * 8/1989 Velez et al. ..... 351/210
4,894,777 A 1/1990 Negishi
4,953,111 A * 8/1990 Yamamoto et al. ..... 340/575
4,967,186 A * 10/1990 Ludmirsky et al. ..... 340/575
4,988,183 A * 1/1991 Kasahara et al. ..... 351/210
5,070,883 A * 12/1991 Kasahara ..... 600/558
5,214,456 A 5/1993 Gersten
5,341,181 A 8/1994 Godard
5,345,281 A 9/1994 Taboada et al.
5,402,109 A * 3/1995 Mannik ..... 340/575
5,447,166 A * 9/1995 Gevins ..... 600/544
5,469,143 A 11/1995 Cooper
5,478,239 A 12/1995 Fuerst
5,481,622 A 1/1996 Gerhardt et al.
5,566,067 A 10/1996 Hobson et al.
5,570,698 A * 11/1996 Liang et al. ..... 600/558
5,583,795 A * 12/1996 Smyth ..... 702/150
5,682,144 A * 10/1997 Mannik ..... 340/575
5,689,241 A * 11/1997 Clarke et al. ..... 340/575
5,704,369 A 1/1998 Scinto
5,726,916 A 3/1998 Smyth
5,748,113 A * 5/1998 Torch ..... 341/21
5,778,893 A 7/1998 Potter
5,795,306 A 8/1998 Shimotani
5,861,936 A * 1/1999 Sorensen ..... 351/200
5,867,587 A * 2/1999 Aboutalib et al. ..... 382/117
5,956,125 A 9/1999 Rosse
6,003,991 A 12/1999 Viirre
6,087,941 A * 7/2000 Ferraz ..... 340/575
6,088,470 A 7/2000 Camus et al.
6,091,378 A 7/2000 Richardson et al.
6,091,546 A 7/2000 Spitzer
6,097,295 A * 8/2000 Griesinger et al. ..... 340/576
6,116,736 A 9/2000 Stark
6,163,281 A * 12/2000 Torch ..... 341/21
6,246,344 B1 * 6/2001 Torch ..... 341/21
6,246,779 B1 6/2001 Fukui
6,247,813 B1 6/2001 Kim
6,252,977 B1 6/2001 Salganicoff et al.
6,334,683 B2 * 1/2002 Apple et al. ..... 351/221
6,373,961 B1 4/2002 Richardson et al.
6,388,639 B1 5/2002 Hoshino
6,611,618 B1 8/2003 Peli
6,775,060 B2 8/2004 Peli et al.
6,820,979 B1 11/2004 Stark
6,864,473 B2 * 3/2005 Chretien et al. ..... 250/201.1
6,997,556 B2 2/2006 Pfleger
7,046,215 B1 5/2006 Bartlett
7,071,831 B2 7/2006 Johns
7,120,880 B1 10/2006 Dryer
7,206,435 B2 4/2007 Fujimura et al.
7,374,284 B2 5/2008 Peli
7,391,888 B2 6/2008 Hu et al.
2001/0028309 A1 10/2001 Torch
2002/0024633 A1 2/2002 Kim
2004/0061680 A1 4/2004 Taboada
2005/0007552 A1 1/2005 Fergason et al.

* cited by examiner

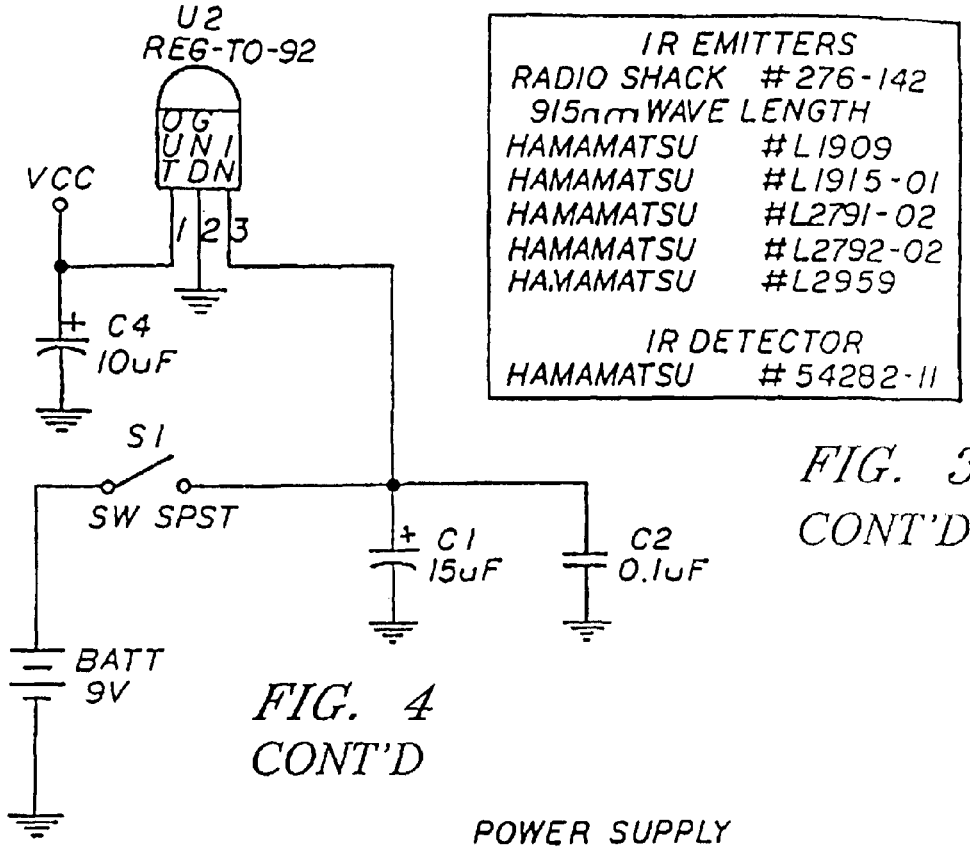
FIG. 3 CONT'D
FIG. 4 CONT'D
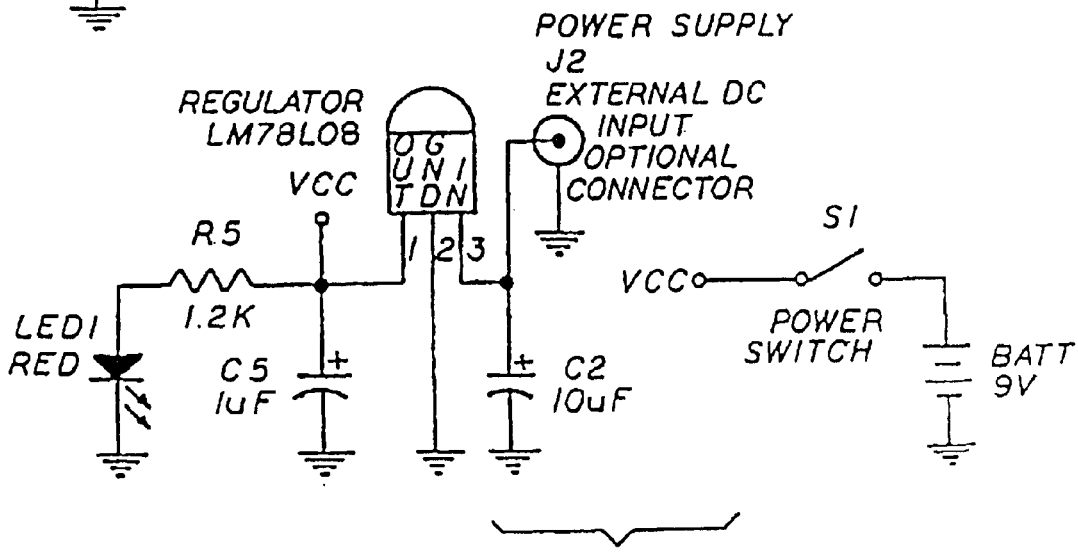
FIG. 3 CONT'D

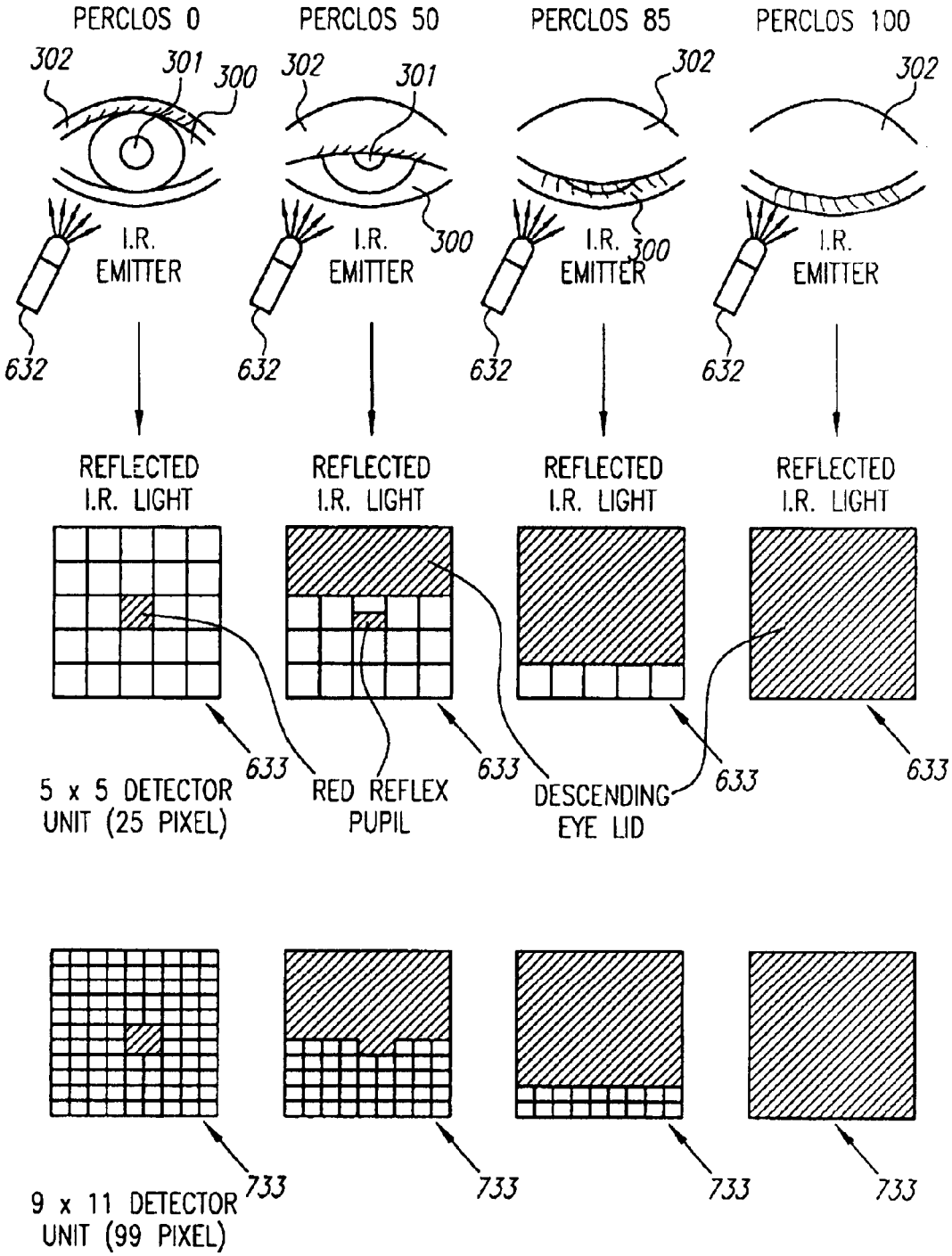
FIG. 12DI FIG. 12DII FIG. 12DIII FIG. 12DIV

SYSTEM AND METHOD FOR MONITORING EYE MOVEMENT

Matter enclosed in heavy brackets [ ] appears in the original patent but forms no part of this reissue specification; matter printed in italics indicates the additions made by reissue.

This application is *a continuation of application Ser. No. 11/097,942, filed Apr. 1, 2005, issued as Re 39,539 on Apr. 3, 2007, which is a reissue of application Ser. No. 09/740,738, U.S. Pat. No. 6,542,081, which is* a continuation-in-part of application Ser. No. 09/104,258, filed Jun. 24, 1998, issuing as U.S. Pat. No. 6,163,281 on Dec. 19, 2000, which is a continuation-in-part of application Ser. No. 08/978,100, filed Nov. 25, 1997, now U.S. Pat. No. 6,246,344 issued Jun. 12, 2001, which is a continuation-in-part of application Ser. No. 08/699,670, filed Aug. 19, 1996, now U.S. Pat. No. 5,748,113 issued May 5, 1998, the disclosures of which are expressly incorporated herein by reference.

*Notice: More than one reissue application has been filed for the reissue of U.S. Pat. No. 6,163,281. The reissue applications are application Ser. No. 11/097,942, issued as Re 39,539, Ser. No. 11/732,828 (the present application), which is a continuation reissue of Re 39,539, and Ser. No. 12/199,693, which is a divisional reissue of the present application.*

FIELD OF THE INVENTION

The present invention relates generally to systems and methods for monitoring movement of a human eye, and more particularly to systems and methods for real-time monitoring of fatigue and other states of mind in individuals, purposeful communication, and/or controlling devices based upon movement of their eye, eyelid, and/or other components of their eye.

BACKGROUND

There have been attempts to use movement of the human eye to monitor involuntary conditions, specifically a person's wakefulness or drowsiness. For example, U.S. Pat. No. 3,863,243 discloses a device that sounds an alarm to warn a person using the device that they are beginning to fall asleep. The device includes a frame similar to a set of eyeglasses onto which is mounted a fiber optic bundle and a photocell that are directed towards the user's eye when the frame is worn. The fiber optic bundle is coupled to a source of light and a pulse generator to emit light towards the user's eye.

The photocell detects the intensity of light reflected off of the user's eye, i.e., either by the eyelid when the eye is closed or the eye surface when the eye is open. Circuitry receives a signal from the photocell, and uses a timer to distinguish between regular blinks, and an extended time period during which the eye is closed, i.e., a time period that may indicate that the person is falling asleep. When a threshold time elapses, an alarm is sounded to notify and/or wake the user. This device, however, requires running wires and fiber optic bundles from the frame to external components, e.g., the pulse generator and the required circuitry, and for this reason, the device may be awkward or inconvenient to use.

Other devices, such as those disclosed in U.S. Pat. Nos. 5,469,143 and 4,359,724, directly engage the eyelid or eyebrow of a user to detect movement of the eye and activate an alarm when a drowsiness condition is detected. These mechanical devices may be mounted directly onto the skin to detect muscle movement or may involve placing a mechanical arm against the eyelid, and consequently may be uncomfortable to wear and use.

In addition, some devices may detect eye movement, but may not be able to distinguish when the eye is opened or closed. For example, it may be desirable to measure the percentage of total time that the eyelids are closed as a function of time or the area of the palpebral fissure that is covered by the eyelid as the eye is opened or closed, commonly known as "PERCLOS," for example during medical research or when monitoring driver alertness. Devices that merely detect eye muscle movement or eyelash movement may not be able to distinguish when the eye is open or closed, and consequently may not be able to measure PERCLOS. Similarly, such devices may not measure other parameters, such as velocity of eyelid closing or opening, acceleration or deceleration characteristics, duration of open or closed eye states, intervals between eye blinks and/or partial versus full eye blinks or eye closures.

Further, infrared cameras or other devices may be used to monitor a driver's awareness, which are typically mounted on the dashboard, roof or other fixed mounting within the user's vehicle. Such devices, however, require that the user maintain constant eye contact with the camera. In addition, they do not monitor eyelid movement if the user looks sideways or downwards, turns around, exits the vehicle or compartment in which he or she is being monitored, or if the camera moves relative to the individual. Further, such cameras may have problems seeing through eyeglasses, sunglasses, or even contact lenses, and may not operate effectively in sunlight.

Accordingly, it is believed that a more effective system and method for monitoring eye and/or eyelid movement would be considered useful.

SUMMARY OF THE INVENTION

The present invention is directed to systems and methods for monitoring eye movement. Generally, humans blink at least about 5–30 times per minute, or about 7,000–43,000 times per day. Each involuntary-reflexive blink lasts about 200–300 milliseconds, and generally averaging about 250 milliseconds, amounting to about 1,750–10,800 seconds per day of eye closure due to involuntary blinking. As tiredness or sleepiness occurs, the eye blink gets longer and slower until the eyes begin to close for short term "microsleeps," i.e., sleep conditions that last for about 3–5 seconds or longer, or for prolonged sleep. The present invention provides systems and methods for monitoring, measuring, and/or responding to eye movement, e.g., nonpurposeful reflexive eyeblinks.

In a preferred embodiment, the system includes an emitter and a sensor in a predetermined relationship with an eye such that the emitter emits light and the sensor detects light from the emitter, the sensor producing a light intensity signal indicating when the eye is open or closed. More preferably, the emitter is directed or aimed at the eyelid and eye, while the sensor detects eyelid-reflected light, since, unlike the eyelid, the eye ball (except the retina, which may cause a "red reflex" under white light conditions or "white pupil" under infrared light) does not reflect substantial light back to the sensor. Circuitry is coupled to the sensor for converting sequential light intensity signals corresponding to eyelid movement received from the sensor into a stream of data, and a processor converts the stream of data into an understandable message.

The circuitry for converting sequential light intensity signals may compare the sequential light intensity signals with a predetermined time threshold to detect voluntary-intentional or unintentional-involuntary sequences of eyelid movements, corresponding, for example, to a predetermined binary code. Memory circuitry may be coupled to the processor for storing the stream of data and/or a communication device, such as a video monitor or synthesized voice module, may be coupled to the processor for communicating the understandable message. In addition, a control system may be coupled to the processor, and the understandable message may include a command for controlling equipment, including electrical or electronic equipment, machinery, or a computer or computer accessory devices coupled to the control system.

The system preferably also includes a transmitter, preferably a radio frequency transmitter, for wireless transmission of the stream of data to a remote location. Alternatively, other forms of wireless transmission, e.g. infrared, as well as hard-wire connections may be used. The processor, as well as the memory circuitry, communication device, and/or control system, may be located at the remote location, and a receiver may be coupled to the processor for receiving the stream of data from the transmitter.

In a preferred form, the system includes a detection device having a frame adapted to be worn on a person's head, e.g., with the frame resting on the bridge of the user's nose and/or ears. The frame has the emitter and sensor thereon such that the emitter and sensor are oriented towards the person's eye when the frame is worn on the person's head. Preferably, the emitter and sensor are a single solid state device, such as a biosensor device, that emits light within a predetermined frequency range, for example infrared light, towards the eye and detects the emitted light reflected off of the eyelid, respectively.

In another preferred embodiment, a system for monitoring a blinking cycle of a person from a remote location is provided that includes an emitter for directing light towards an eye, and a sensor in a predetermined relationship with the emitter for detecting the emitted light reflected off of the eye, the sensor producing an output signal indicating when the eye is open or closed. Depending upon the relative position of the emitter and sensor with respect to the moving eyelid, the emitter light may be reflected off of the eyelid back to the sensor, or diffused by the surface of the eyeball.

A transmitter is coupled to the sensor for wireless transmission of the output signal, and a processor is provided for comparing the output signal to a predetermined threshold to detect when the eyelid is closed for a minimum predetermined duration. A warning indicator may be coupled to the processor, the warning indicator being activated when the processor detects that the eyelid is closed for the minimum predetermined duration. For example, the warning indicator may be an audible buzzer, a visible warning light, a vibrating device, an electrical shock device, a gustatory smell device, or other device that may act as a stimulus to any sensory modality.

Similar to the previous embodiment, a receiver may be provided at the remote location coupled to the processor for receiving the wireless transmission from the transmitter. Memory circuitry may be provided for storing the output signal and/or a processor may be provided for converting the output signal into an understandable message. A communication device may be coupled to the processor for communicating the understandable message.

In another preferred embodiment, a self-contained device for detecting movement of a person's eyelid is provided that includes a frame adapted to be worn on the person's head, an emitter on the frame for directing light towards an eye of the person when the frame is worn, and a sensor on the frame for detecting light from the emitter. The sensor produces an output signal indicating when the eye is open or closed, and a transmitter on the frame is coupled to the sensor for wireless transmission of the output signal to a remote location. The frame may also include a processor for comparing the output signal to a predetermined threshold to detect drowsiness-induced eyelid movement. Similar to the previous embodiments, the emitter and sensor are preferably a solid state biosensor device for emitting and detecting infrared light, or alternatively an array of emitters and/or sensors in a predetermined configuration on the frame, e.g., in a vertical, horizontal, diagonal, or other linear or other geometric array of more than one emitter and/or sensor oriented towards one or both eyes. In particular, an array of emitters and/or sensors allows measurement of eyelid velocity, acceleration and deceleration, and calculation of "PERCLOS."

The emitter and/or sensors may be affixed to any number of points on the frame, e.g., around the lens and preferably in the nose bridge, or alternatively anywhere along the frame, including near or on the nasal portion of the frame, the attachment of a temple piece of the frame, and/or surface mounted on the lens of an eyeglass. Alternatively, the emitter and/or sensor may be embedded in the lens of an eyeglass, or otherwise such that they operate through the lens. Thus, the emitter(s) and/or sensor(s) are fixed on an eye-frame such that they move with the wearer's head movements, and continuously focus on the user's eyes, whether the user is in a vehicle, outdoors or in any other environment.

Thus, a system in accordance with the present invention may detect eyelid movement of the user, distinguish normal blinks from other voluntary or involuntary eyelid movement, and produce a stream of data. The stream of data may be converted into an understandable message, such as a binary code, a command for controlling a piece of equipment, or an indicator of the user's physical, mental or emotional state. Thus, the system may provide a convenient and/or effective method for voluntary or involuntary communication based simply upon movement of the user's eye.

In accordance with another aspect of the present invention, a system is provided for monitoring movement of a person's eye. The system includes a device configured to be worn on a person's head and an array of emitters on the device for directing light towards an eye of the person when the device is worn. The array of emitters is configured for projecting a reference frame towards the eye. A camera is oriented towards the eye for monitoring movement of the eye relative to the reference frame. The camera may be provided on the device or may be provided remote from the device, but in relatively close proximity to the user.

Preferably, the array of emitters includes a plurality of emitters disposed in a substantially vertical arrangement on the device, and a plurality of emitters disposed in a substantially horizontal arrangement on the device. Thus, the array of emitters may project a focused set of crossed bands towards the eye for dividing a region including the eye into four quadrants.

In addition, the system preferably includes one or more scanning or nonscanning sensors on the device for detecting light from the array of emitters. The one or more sensors produce an output signal indicating when the eye is open or closed, similar to the embodiments described above. More preferably, the sensors include an array of focused sensors in a predetermined relationship with the array of focused emitters for detecting light from the array of emitters that is reflected off of respective portions of the eye or its eyelid. The emitters, because of their fixed position, produce a fixed reflection off of the surface of the eye and eyelid, appearing as a "glint," i.e., a spot or band of light. Each sensor produces an output signal indicating when the respective portion of the eye is covered or not covered by the eyelid.

The system may also include a processor for correlating the output signal from the one or more sensors with a video signal from the camera for determining the person's level of alertness. The system may also include a warning indicator on the device, the warning indicator being activated when the processor determines a predetermined level of drowsiness has occurred.

Light from the array of emitters may be emitted towards the eye of a user wearing the device to project a reference frame onto the eye. The camera is capable of imaging light produced by the emitters, e.g., in the infrared light range, thereby detecting the projected light as a spot of light, band of light or other "glint." Movement of the eye relative to the reference frame may be monitored with the camera. A graphical output of the movement monitored by the camera relative to the reference frame may be monitored. For example, infrared light from the emitters may be reflected off of the retina as a "red reflex" under white light, as a "white pupil" under infrared light, or as a dark pupil under subtraction, using methods known to those skilled in the art. The processor, using these methods, may detect movement of the eye's pupil [may be measured] relative to the reference frame. This movement may be graphically displayed, showing the movement of the eye's pupil relative to the reference frame.

In addition, the output signal from the one or more sensors may be correlated with video signals produced by the camera monitoring movement of the eye relative to the reference frame, thereby determining the person's level of drowsiness.

Other objects and features of the present invention will become apparent from consideration of the following description taken in conjunction with the accompanying drawings.

BRIEF DESCRIPTION OF THE DRAWINGS

FIG. 12D is a table showing the relationship between the activation of two-dimensional arrays of sensors and an eye being monitored, as the eye progresses between open and closed conditions.

DETAILED DESCRIPTION OF THE PREFERRED EMBODIMENTS

Figure 1:
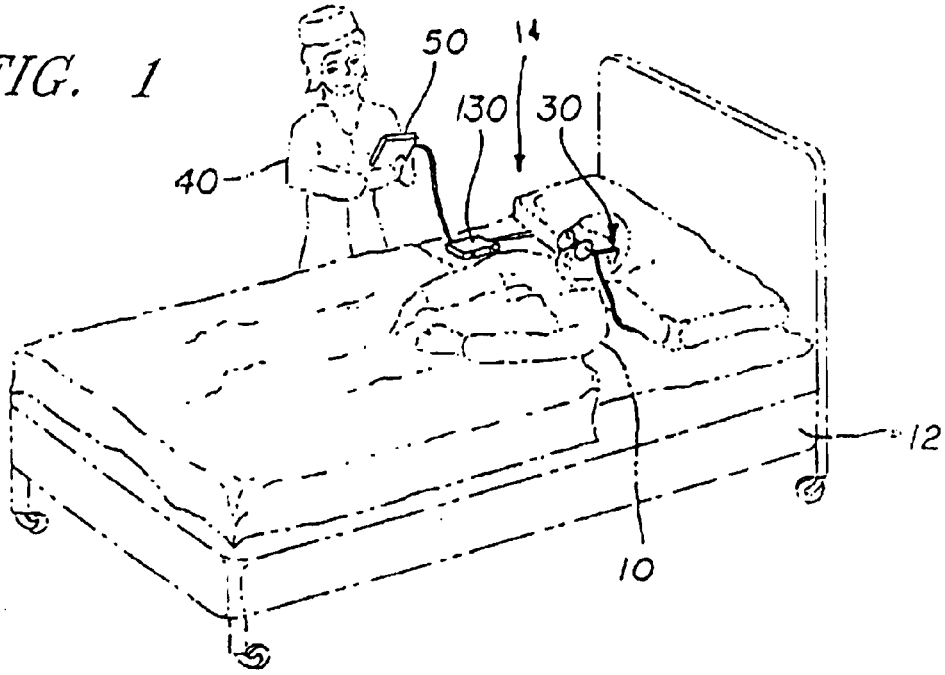
FIG. 1 is a perspective view of a patient in a hospital wearing a system for communication using eyelid movement in accordance with the present invention.

Turning now to the drawings, FIG. 1 shows a patient 10 in a bed 12 wearing a detection device 30 for detecting eyelid movement of the patient 10 to provide voluntary-purposeful and/or involuntary-nonpurposeful communication. The detection device 30 is coupled to a processing box 130 which converts the detected eyelid movement into a stream of data, an understandable message and/or into information, which may be communicated, for example, using a video display 50, to a medical care provider 40. The detection device 30 and processing box 130 together provide a system for communication 14 in accordance with one aspect of the present invention.

Figure 2:
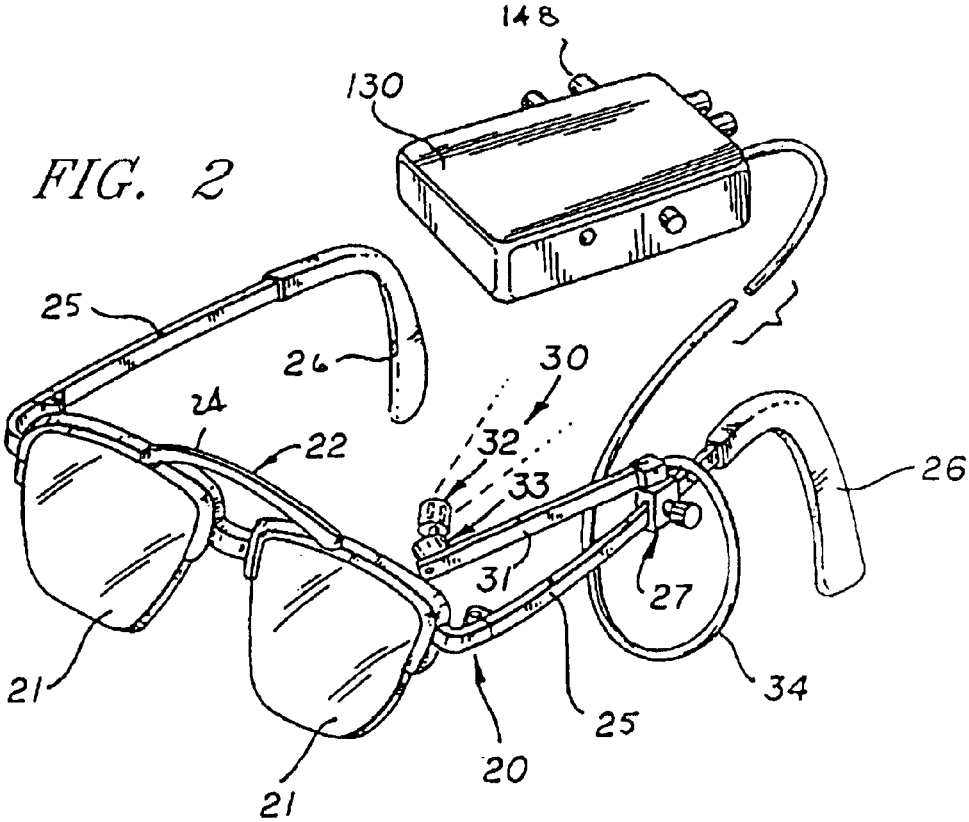
FIG. 2 is an enlarged perspective view of a preferred embodiment of the system for communication using eyelid movement, shown in FIG. 1, including a detection device and a processing box.
Figure 6A:
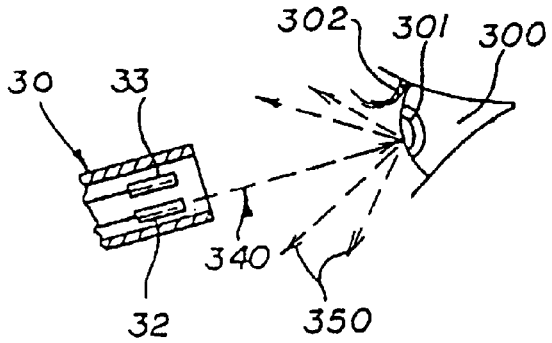
FIGS. 6A–6C are sectional and front views of alternate embodiments of a device for emitting light towards and detecting light reflected from a surface of an open eye.
Figure 7A:
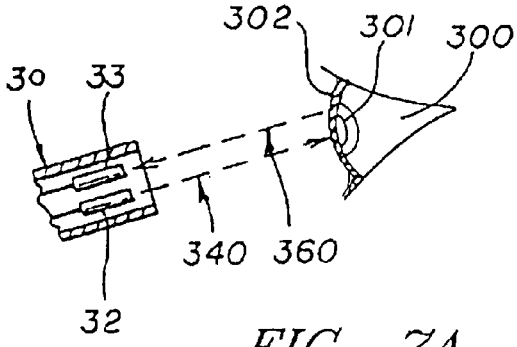
FIGS. 7A–7C are sectional and front views of the devices of FIGS. 6A–6C, respectively, emitting light towards and detecting light reflected from a closed eyelid.

Turning to FIGS. 2, 6A and 7A, a preferred embodiment of a system for communication 14 is shown that includes an aimable and focusable detection device 30 that is attachable to a conventional pair of eyeglasses 20. The eyeglasses 20 include a pair of lenses 21 attached to a frame 22, which includes bridgework 24 extending between the lenses 21, and side members or temple pieces 25 carrying ear pieces 26, all of which are conventional. Alternatively, because the lenses 21 are not necessary to the present invention, the frame 22 may also be provided without the lenses 21.

The detection device 30 includes a clamp 27 for attaching to one of the side members 25 and an adjustable arm 31 onto which is mounted an emitter 32 and a sensor 33. Preferably, the emitter 32 and sensor 33 are mounted in a predetermined relationship such that the emitter 32 may emit a signal towards an eye 300 of a person wearing the eyeglasses 20 and the sensor 33 may detect the signal reflected from the surface of the eye 300 and eyelid 302. As shown in FIGS. 6A and 7A, the emitter 32 and sensor 33 may be mounted adjacent one another.

Figure 6B:
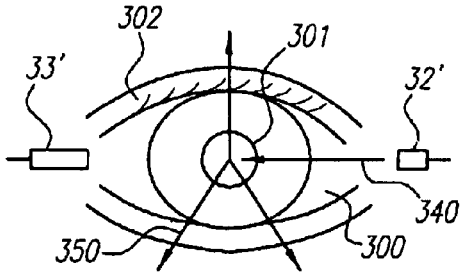
Figure 7B:
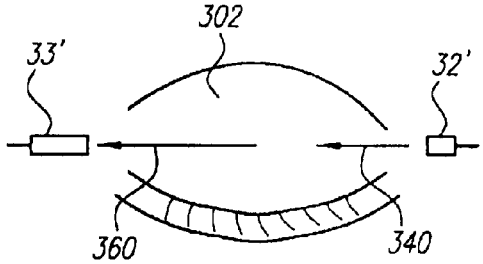
Figure 6C:
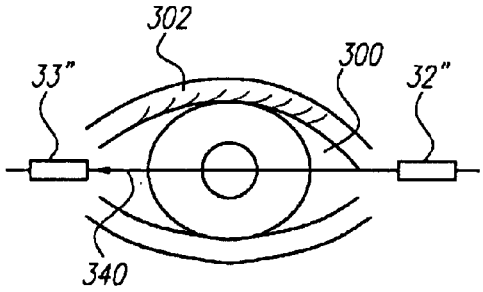
Figure 7C:
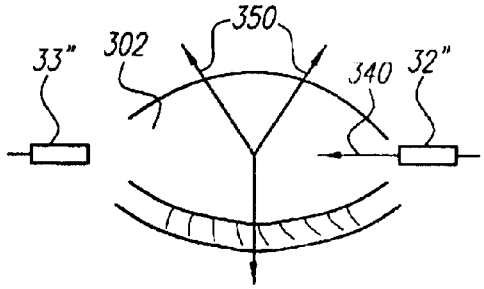

Alternatively, as shown in FIGS. 6B and 7B, the emitter 32' and sensor 33' may be mounted on the frame separately away from one another, preferably such that the emitter 32' and sensor 33' are disposed substantially laterally with respect to each other. In a further alternative, shown in FIGS. 6C and 7C, the emitter 32" and sensor 33" may be mounted across the eye 300 in axial alignment with another. As the eyelid 302 closes, it may break the beam 340 being detected by the sensor 33".

In a preferred form, the emitter 32 and sensor 33 produce and detect continuous or pulsed light, respectively, preferably within the infrared range to minimize distraction or interference with the wearer's normal vision. Preferably, the emitter 32 emits light in pulses at a predetermined frequency and the sensor 33 is configured to detect light pulses at the predetermined frequency. This pulsed operation may reduce energy consumption by the emitter 32 and/or may minimize interference with other light sources. Alternatively, other predetermined frequency ranges of light beyond or within the visible spectrum, such as ultraviolet light, or other forms of energy, such as radio waves, sonic waves and the like, may be used.

Figure 3:
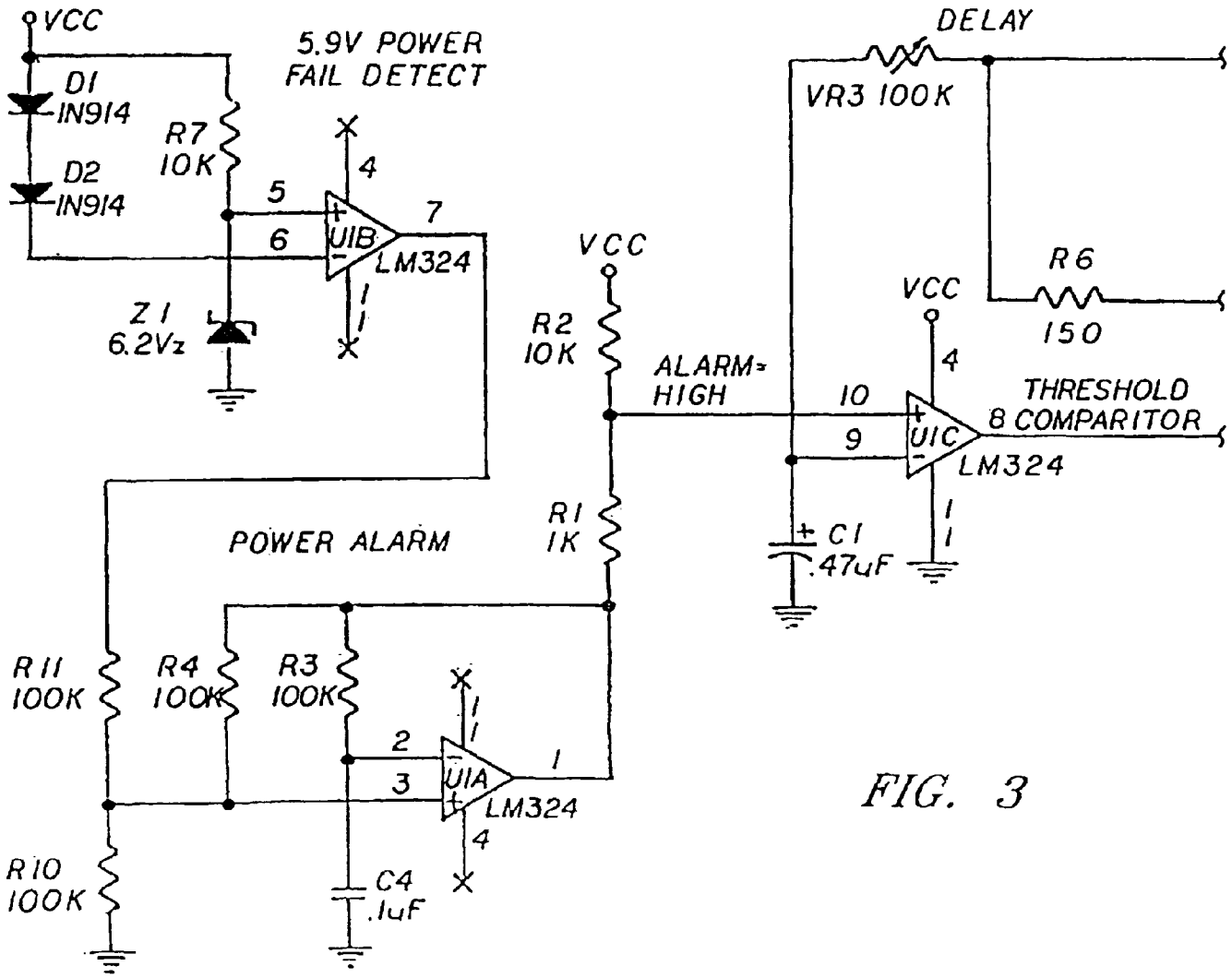
FIG. 3 is a schematic drawing of a preferred embodiment of circuitry for transmitting an output signal corresponding to a sequence of eyelid movements.
Figure 3:
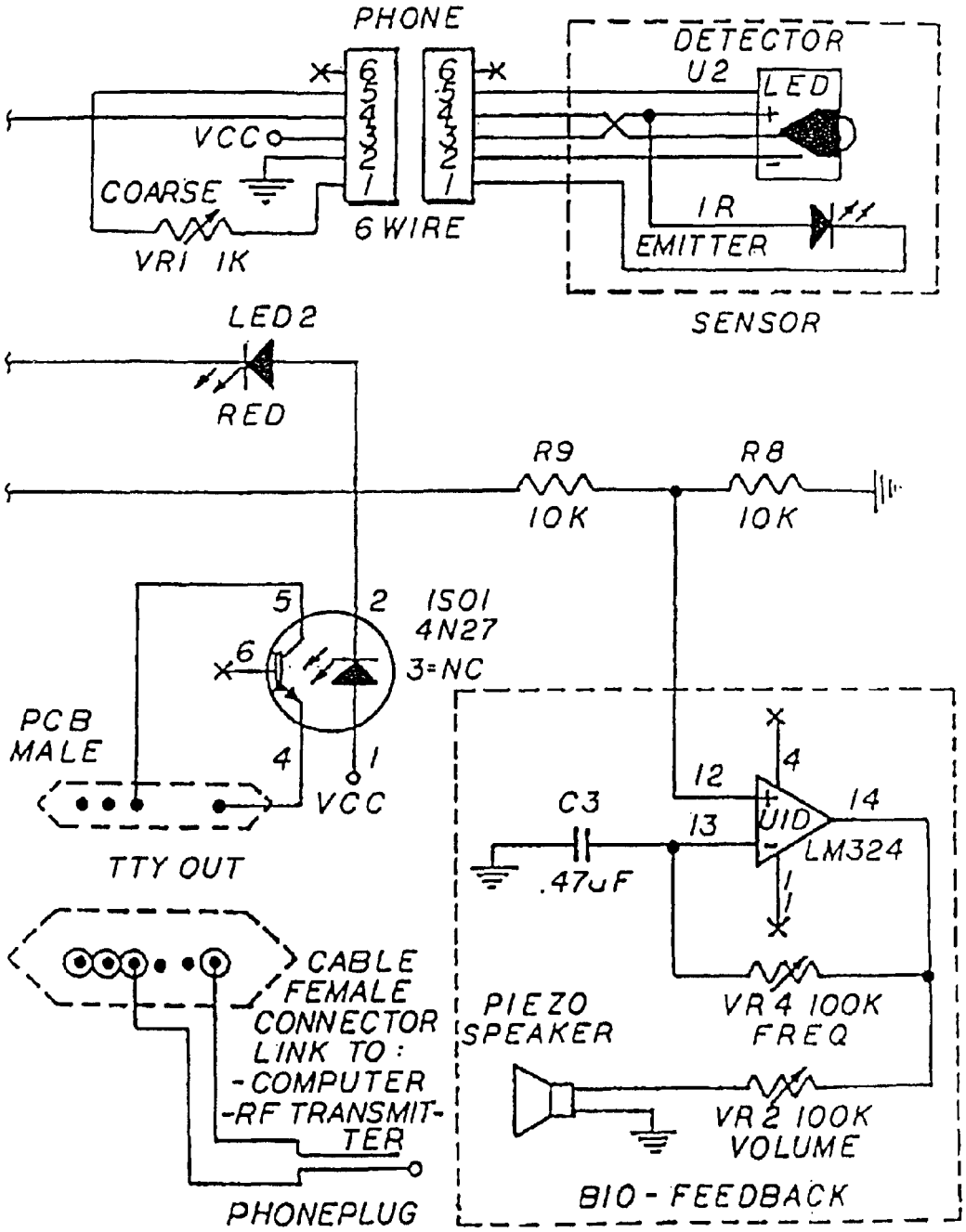
Figure 4:
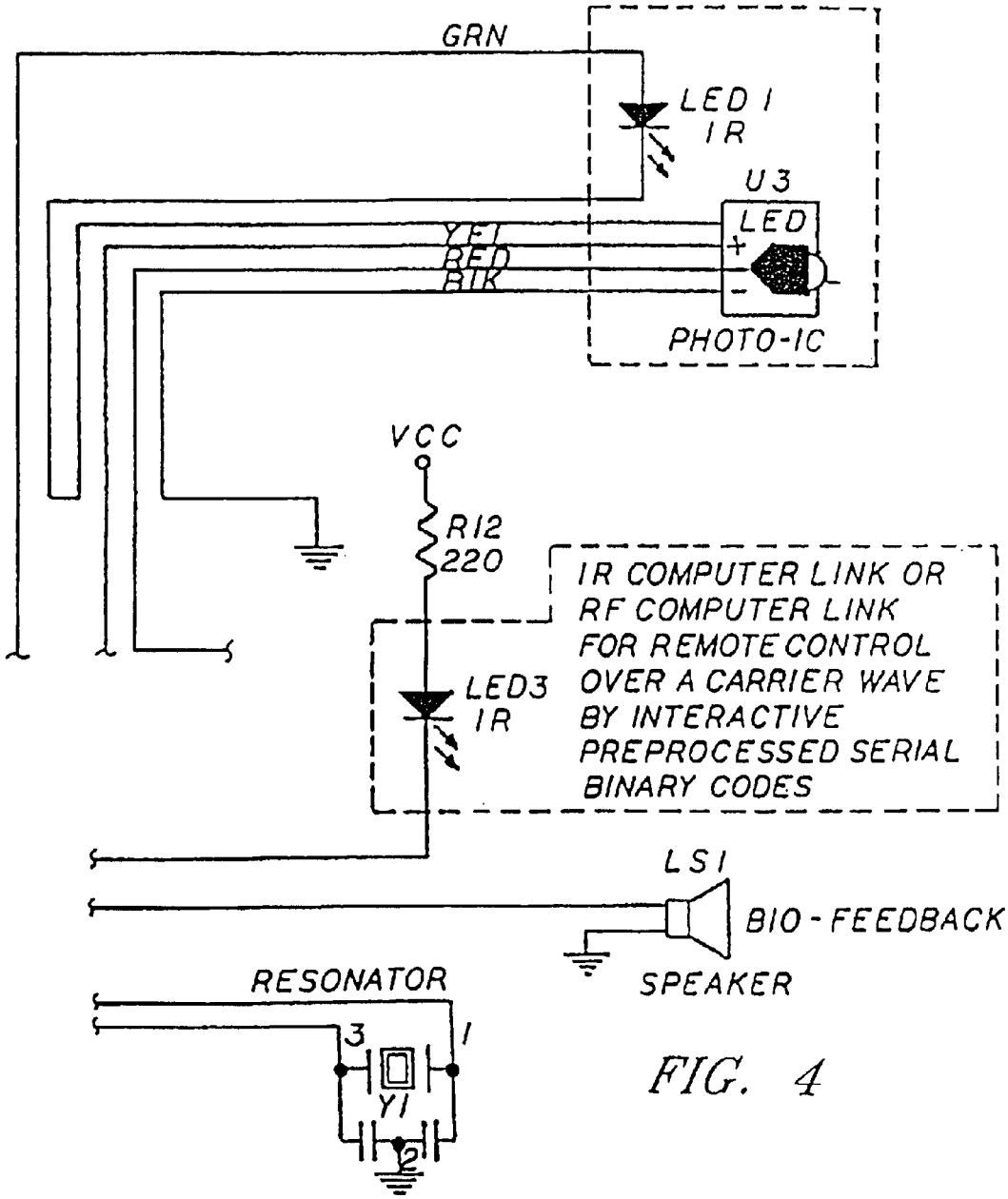
FIG. 4 is a schematic drawing of a preferred embodiment of circuitry for controlling equipment in response to an output signal corresponding to a sequence of eyelid movements.
Figure 4:
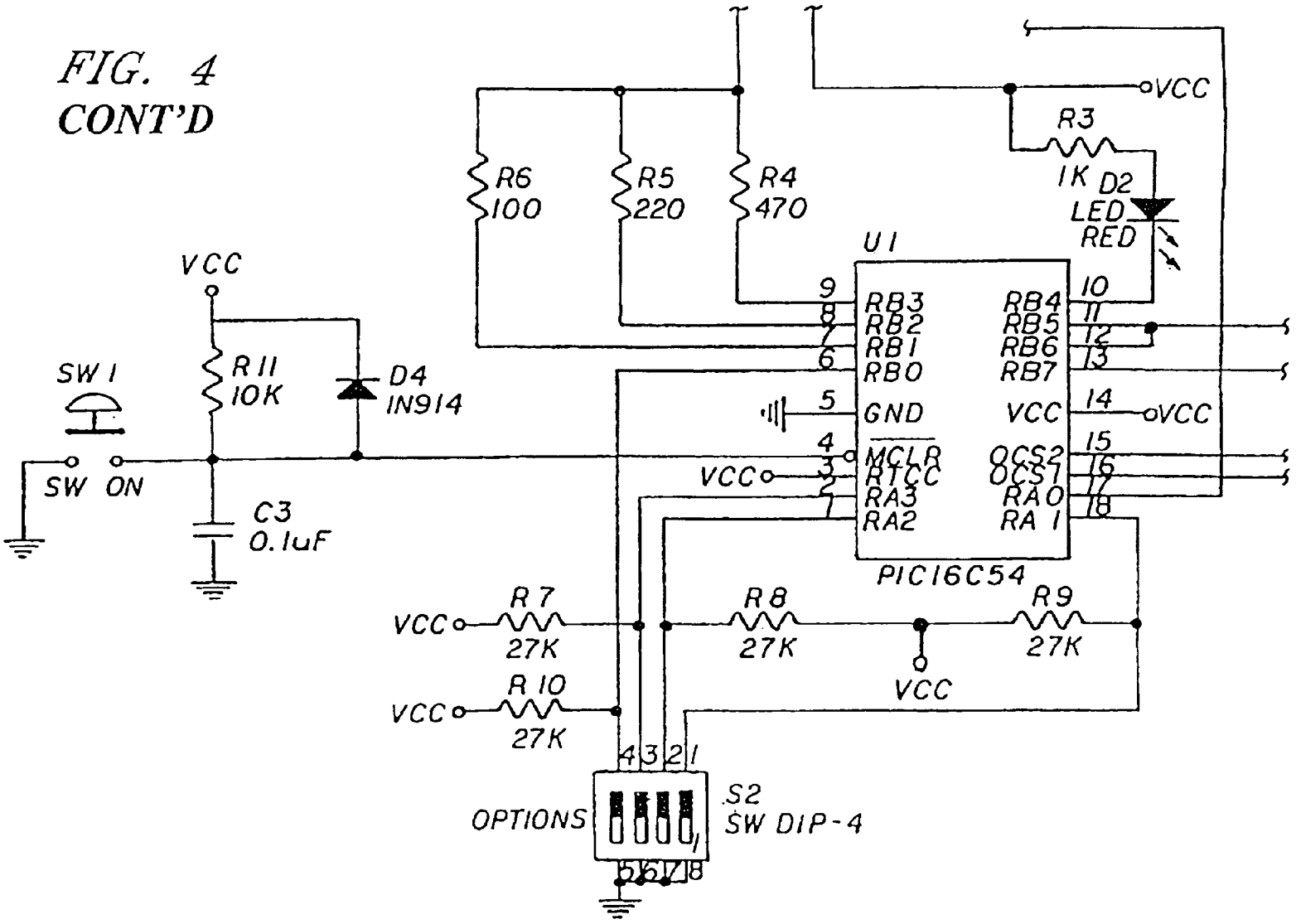
Figure 5:
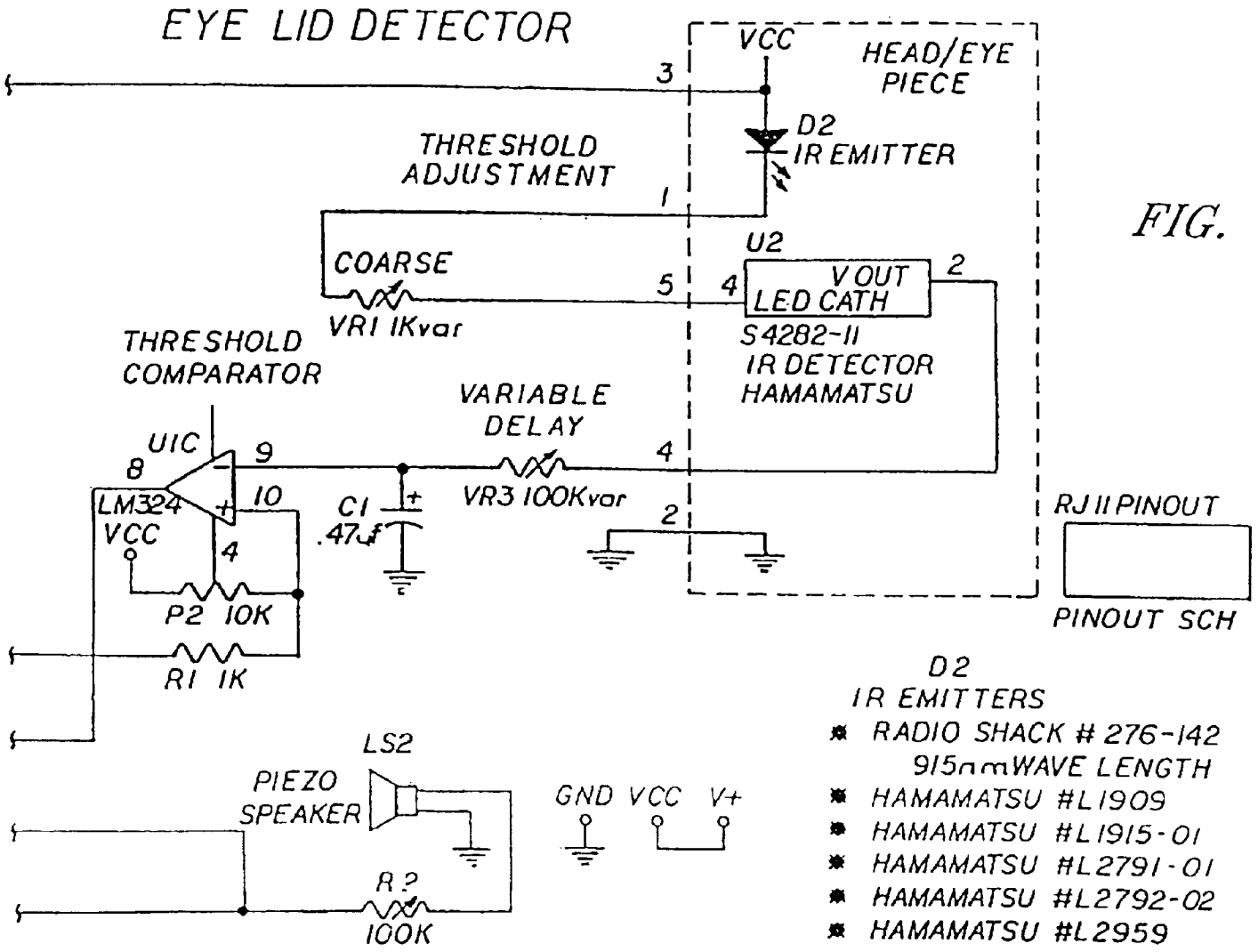
FIG. 5 is a schematic drawing of a preferred embodiment of circuitry for detecting eyelid movement.
Figure 5:
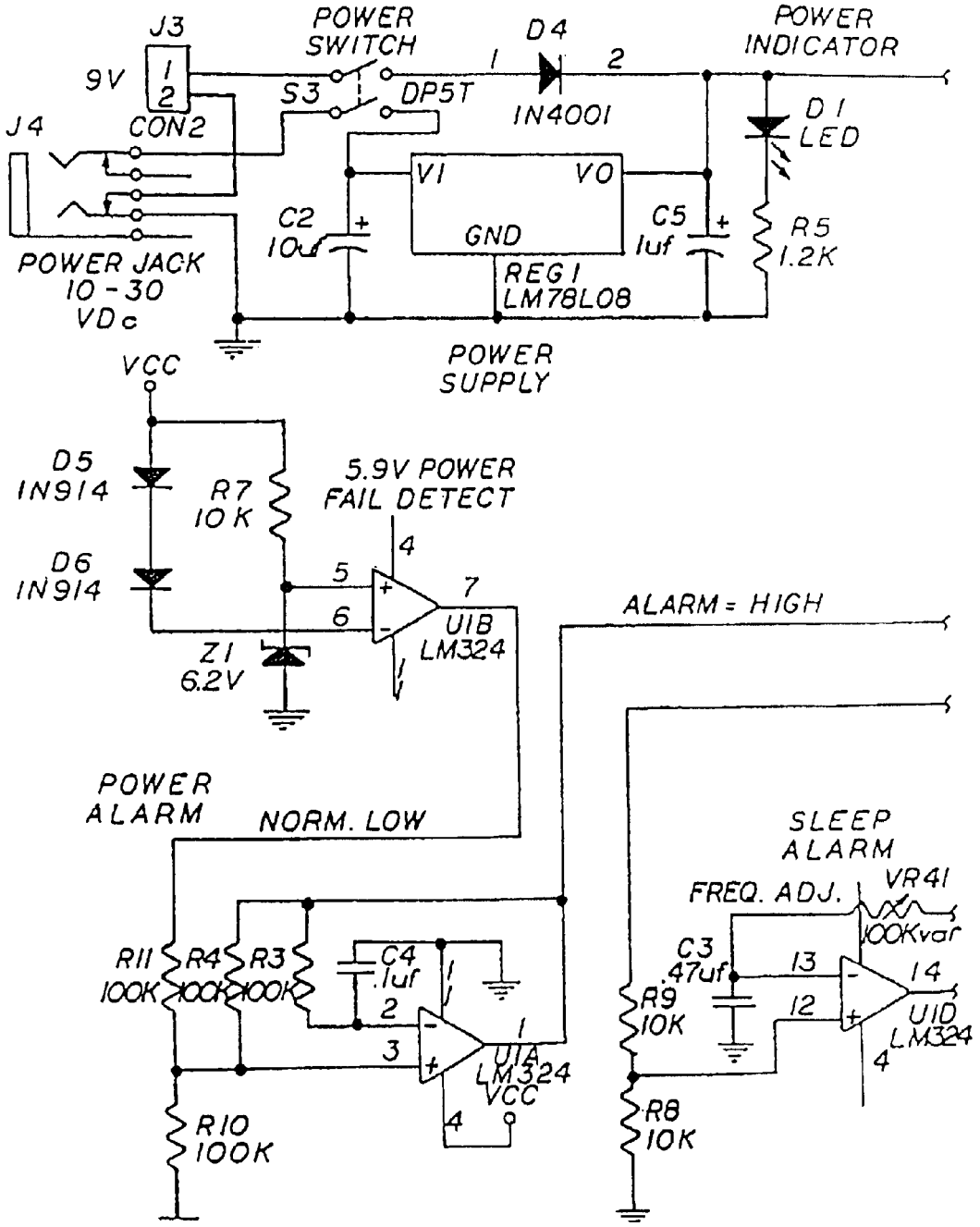
Figure 9:
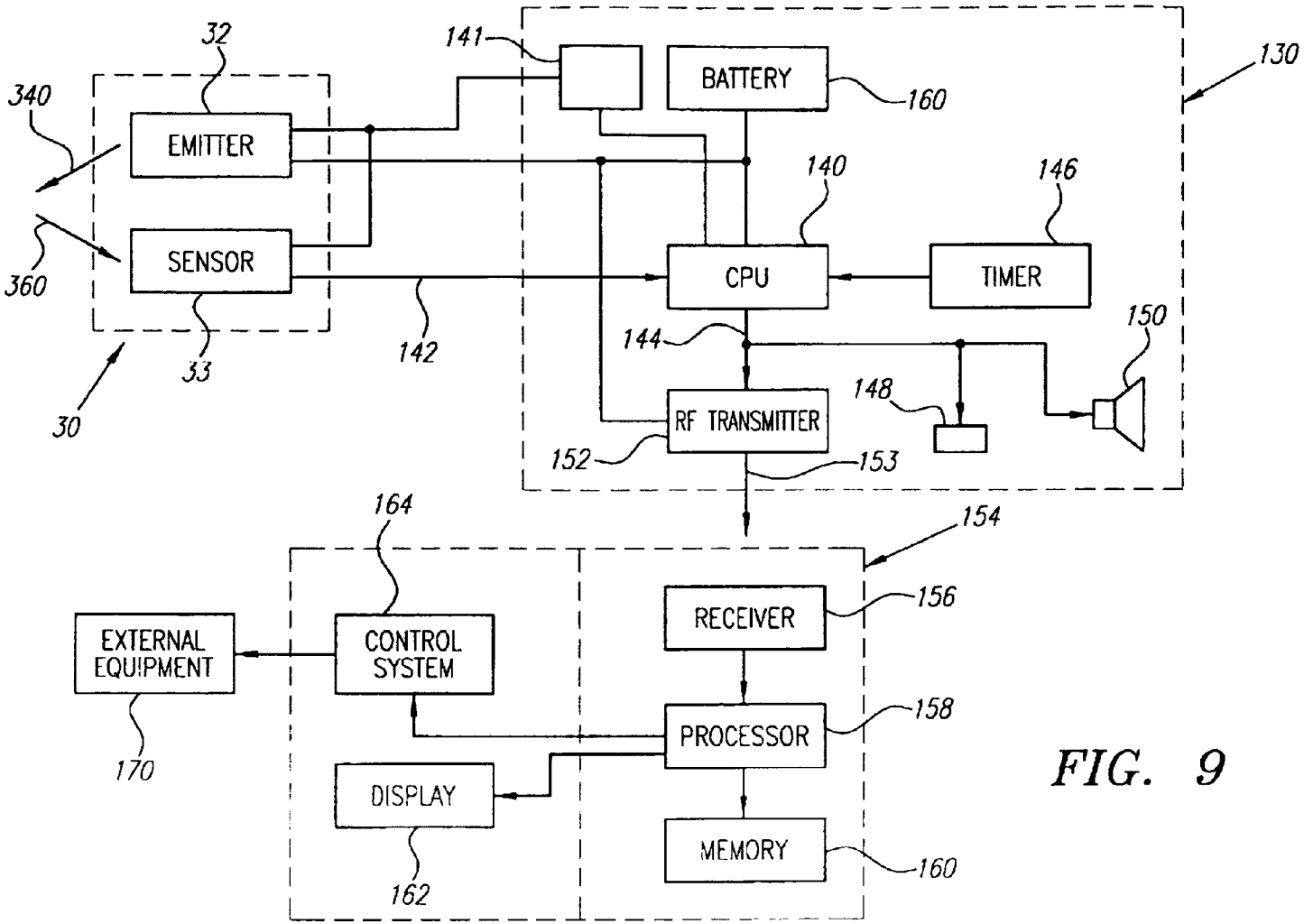
FIG. 9 is a block diagram of the components of a system for communication in accordance with the present invention.

The processing box 130 is coupled to the detection device 30 by a cable 34 including one or more wires therein (not shown). As shown in FIG. 9, the processing box 130 preferably includes a central processing unit (CPU) 140 and/or other circuitry, such as the exemplary circuitry shown in FIGS. 3–5, for receiving and/or processing an output signal 142, such as a light intensity signal, from the sensor 33. The processing box 130 may also include control circuitry 141 for controlling the emitter 32 and/or the sensor 33, or the CPU 140 may include internal control circuitry.

For example, in a preferred form, the control circuitry 141 controls the emitter 32 to produce a flickering infrared signal pulsed at a predetermined frequency, as high as thousands of pulses per second to as little as about 4–5 pulses per second, and preferably at least about 5–20 pulses per second, thereby facilitating detection of nonpurposeful or purposeful eyeblinks as short as about 200 milliseconds per blink. The sensor 33 may be controlled to detect light pulses only at the predetermined frequency specific to the flicker frequency of the emitter 32. Thus, by synchronizing the emitter 32 and the sensor 33 to the predetermined frequency, the system 10 may be used under a variety of ambient conditions without the output signal 142 being substantially affected by, for example, bright sun light, total darkness, ambient infrared light backgrounds, or other emitters operating at different flicker frequencies. The flicker frequency may be adjusted to minimize the efficient measurement of the number of eye blinks per unit time (e.g. about ten to about twenty eye blinks per minute), the duration of each eye blink (e.g. about 200 milliseconds to about 300 milliseconds), and/or PERCLOS (i.e., the percentage of time that the eyelid is completely or partially closed), or to maximize efficiency of the system, while keeping power consumption to a minimum.

The control circuitry 141 and/or processing box 130 may include manual controls (not shown) for adjusting the frequency, focus, or intensity of the light emitted by the emitter 32, to turn the emitter 32 off and on, to adjust the threshold sensitivity of the sensor 33, and/or to allow for self-focusing with maximal infrared reflection off of a closed eyelid, as will be appreciated by those skilled in the art.

In addition, the processing box 130 also preferably includes a power source 160 for providing power to the emitter 32, the sensor 33, the CPU 144, and/or other components in the processing box 130. The processor box 130 may be powered by a conventional DC battery, e.g., a nine volt battery or a lithium battery. Alternatively, an adapter (not shown) may be connected to the processor box 130, such as a conventional AC adapter or a twelve volt automobile lighter adapter.

Preferably, the CPU 140 includes timer circuitry 146 for comparing the length of individual elements of the output signal 142 to a predetermined threshold to distinguish between normal blinks and other eyelid movement. The timer circuitry 146 may be separate discrete components or may be provided internally within the CPU 140, as will be appreciated by those skilled in the art. The CPU 140 converts the output signal 142 into a stream of data 144 which may be used to communicate to other persons or equipment. For example, the stream of data 144 produced by the CPU 140 may be a binary signal, such as Morse code or ASCI code. Alternatively, the CPU 140 may be capable of producing a synthesized voice signal, a control signal for a piece of equipment, or even a pictorial representation.

To facilitate communication, the processing box 130 may include a variety of output devices for using the stream of data 144. For example, an internal speaker 150 may be provided, which may produce an alarm sound or a synthesized voice. An output port 148 may be provided to which a variety of equipment, such as the video display 50 shown in FIG. 1, may be directly coupled by hard-wire connections.

The processing box 130 may also include a transmitter 152 coupled to the CPU 144 for wireless communication of the stream of data 144 to a remote location. For example, as shown in FIG. 9, the system for communication 14 may also include a receiving and processing unit 154, such as a computer or other control or display system. The transmitter 152 is preferably a radio frequency transmitter capable of producing a short range signal, for example, reaching as far as about one hundred feet or more, and preferably about forty five feet to fifty feet, even through walls or obstacles, although alternatively an infrared transmitter may also be effective.

The transmitter 152 may also be coupled to an amplifier (not shown) to allow the stream of data to be transmitted thousands of feet or more. For example, the amplifier and transmitter 152 may communicate via telephone communication lines, satellites and the like, to transmit the stream of data to a remote location miles away from the system. The system may include, or may be coupled to a global positioning system (GPS) for monitoring the location, movement, and state of wakefulness and safety of an individual wearing the detection device 30.

The receiving and processing unit 154 includes a receiver 156, preferably a radio frequency receiver, for receiving a signal 153, including the stream of data, transmitted by the transmitter 152. A processor 158 is coupled to the receiver 156 for translating, storing and/or using the information in the stream of data, the processor 158 being coupled to memory circuitry 160, a communication device 162, and/or a control system 164. For example, the receiving and processing unit 154 may include the memory circuitry 160 therein into which the processor 158 may simply store the stream of data for subsequent retrieval and analysis.

The processor 158 may interpret the stream of data, for example, by converting a binary code in the stream of data into an understandable message, i.e., a series of letters, words and/or commands, and/or may use augmentative communication devices or software (such as KE:NX or Words Plus) to facilitate communication. The resulting message may be displayed on the communication device 162, which may include a video display for displaying text, pictures and/or symbols, a synthesized voice module for providing electronic speech, and the like.

Figure 12A:
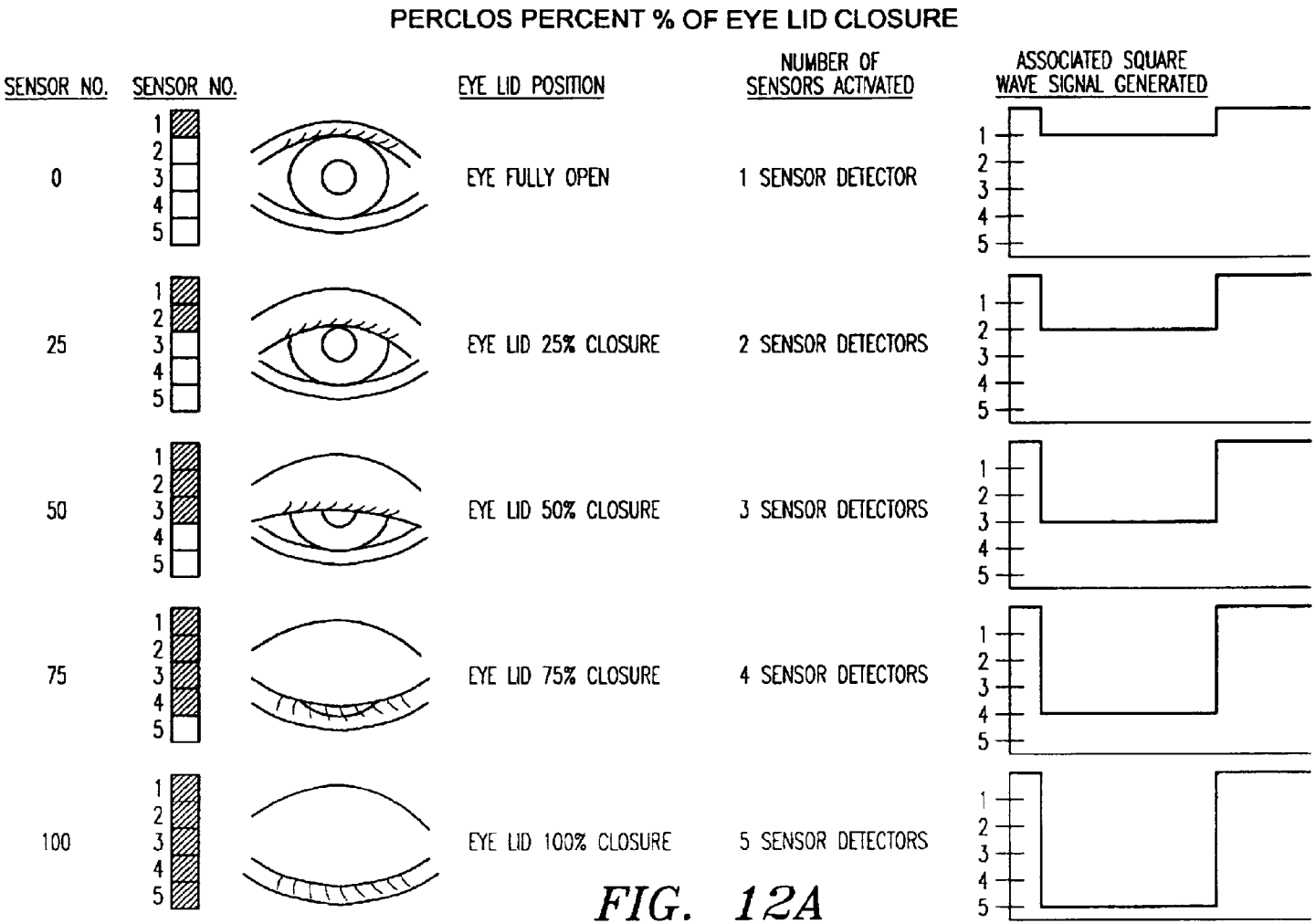
FIG. 12A is a table showing the relationship between the activation of an array of sensors, such as that shown in FIGS. 10A–10D and an eye being monitored by the array, as the eye progresses between open and closed conditions.

Alternatively, the stream of data may be displayed graphically on a computer of video screen or other electronic display device as a "real time" message signal or numerically (e.g., displaying blink rate, blink duration, PERCLOS, etc.), or displayed graphically similar to an EKG or EEG tracing. In addition, as shown in FIG. 12C, the stream of data may be displayed along with other physiological data (e.g. heart rate, respiratory rate, other sleep polysomnographic (PSG) or electroencephalographic (EEG) variables). Alternatively, the stream of data may be integrated with controllers which monitor automobile or mechanical functions (e.g. vehicle speed, acceleration, braking functions, torque, sway or tilt, engine or motor speed, etc.) to make intelligent decisions regarding slowing down or speeding up the vehicle depending upon road and/or vehicle conditions, as well as the state of consciousness, wakefulness or attentiveness of the driver or machine operator.

In addition, the message may be interpreted by the processor 158 for directing the control system 164 to control one or more pieces of machinery or equipment. For example, the stream of data may include a command to direct the control system 164 to control relay switches or other devices to turn off and on an electrical device, such as an appliance, electrical wheelchair, engine, light, alarm, telephone, television, computer, a tactile vibrating seat, and the like, or to operate an eye-activated computer mouse or other controller.

Alternatively, the processor 158 may use the stream of data to control PC, IBM, Macintosh and other computers and compatible computer software and/or hardware, e.g., to interact with a computer similar to a mouse, a "return" key or a "joystick." For example, the stream of data may include commands to activate a series of menus from which submenus or individual items may be selected, as are used in commercially available special communications software, such as WORDS-PLUS or Ke:NX. The processor 158 may then control, scroll or select items from computer software programs, operate a printer or other peripheral device (e.g., selecting a font, paragraph, tab or other symbol operator, selecting commands, such as "edit," "find," "format," "insert," "help," or controlling CD-ROM or disc drive operations, and/or other Windows and non-Windows functions).

Alternatively, the receiver 156 may be coupled directly to a variety of devices (not shown), such as radio or television controls, lamps, fans, heaters, motors, remote control vehicles, vehicle monitoring or controlling devices, computers, printers, telephones, lifeline units, electronic toys, or augmentative communication systems, to provide a direct interface between the user and the devices.

During use, the detection device 30 is placed on a user's head, i.e., by putting the eyeglasses 20 on as shown in FIG. 1. The adjustable arm 31 and/or the clamp 27 may be adjusted to optimally orient the emitter 32 and sensor 33 towards the user's eye 300 (shown in FIGS. 6A–6C and 7A–7C). The emitter 32 is activated and a beam of light 340 is directed from the emitter 32 towards the eye 300. The intensity and/or frequency of the emitter 32 and/or the threshold sensitivity of the sensor 33 or other focus may then be adjusted (e.g. manually or automatically using self-adjusting features).

Because of the difference in the reflective characteristics of the surface of the eye 300 itself and the eyelid 302, the intensity of the light reflected off of the eye 300 depends upon whether the eye 300 is open or closed. For example, FIGS. 6A and 6B illustrate an open eye condition, in which a ray of light 340 produced by the emitter 32 strikes the surface of the eye 300 itself and consequently is scattered, as shown by the rays 350. Thus, the resulting light intensity detected by the sensor 33 is relatively low, i.e., the sensor 33 may not receive any substantial return signal.

In FIGS. 7A and 7B, the eye 300 is shown with the eyelid 302 closed as may occur during normal blinks, moments of drowsiness, intentional blinks, or other eyelid movement. Because the light 340 strikes the eyelid 302, it is substantially reflected back to the sensor 33, as shown by the ray 360, resulting in a relatively high light intensity being detected by the sensor 33. Alternatively, as shown in 7C, the beam of light 340 may be broken or cut by the eyelid 302 when the eye 300 is closed.

The sensor 33 consequently produces a light intensity signal that indicates when the eye 300 is open or closed, i.e., corresponding to the time during which reflected light is not detected or detected, respectively, by the sensor 33. Generally, the intensity of the infrared light reflected from the surface of the eyelid is not substantially affected by skin pigmentation. If it is desired to adjust the intensity of light reflected from the eyelid, foil, glitter, reflective moisturizer creams and the like may be applied to increase reflectivity, or black eye liner, absorptive or deflective creams and the like may be applied to reduce reflectivity.

Figure 12B:
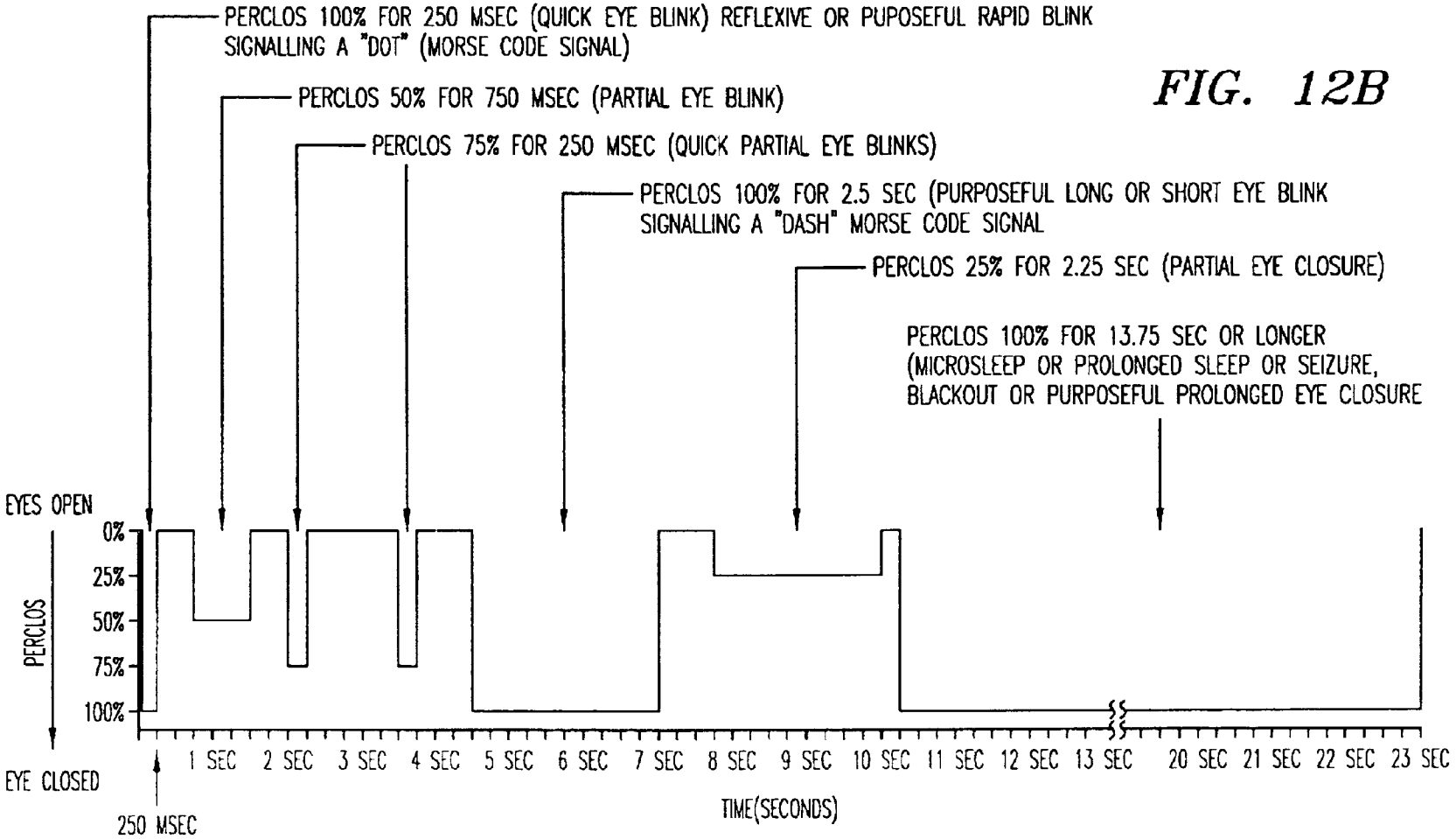
FIG. 12B is a graph showing a stream of data provided by an array of sensors, such as that shown in FIGS. 10A–10D, indicating the percentage of eye coverage as a function of time ("PERCLOS").
Figure 12C:
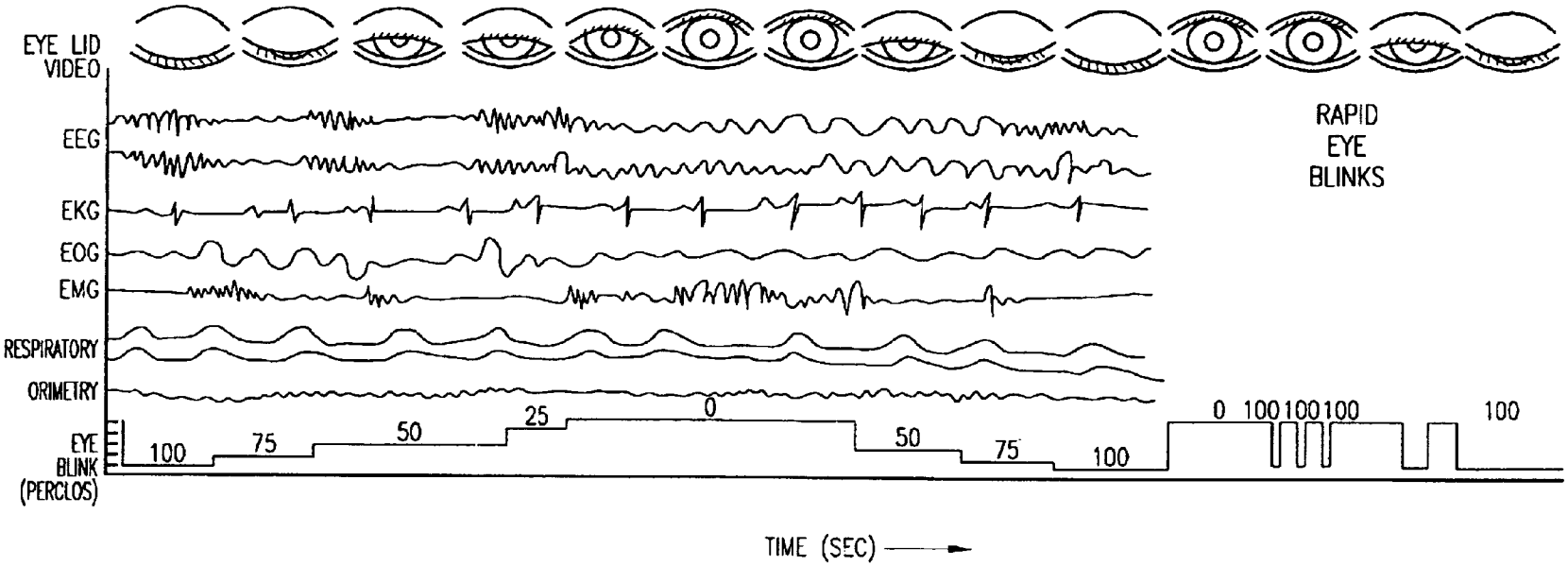
FIG. 12C is a graphical display of a number of physiological parameters, including PERCLOS, of a person being monitored by a system including a device such as that shown in FIGS. 10A–10D.

Returning to FIG. 9, the light intensity detected by the sensor 33 results in an output signal 142 including a series of time-dependent light intensity signals (as shown, for example, in FIG. 12B). The output signal 142 is received by the CPU 140 coupled to the sensor 33, which compares the length of time of each light intensity signal 142, for example, corresponding to a closed eye condition, with a predetermined threshold. The timer circuitry 146 may provide a threshold time to the CPU 140 for distinguishing normal blinks from intentional and/or other unintentional eyelid movement, which the CPU 140 may then filter out of the output signal 142. The CPU 140 then produces a stream of data 144 which may be used for voluntary and/or involuntary communication.

In one useful application, the detection device 30 may be used to detect impending drowsiness or "micro-sleeps" (i.e., sleep intrusions into wakefulness lasting a few seconds) of a user, with the processing box 130 triggering a warning to alert the user, others in his or her presence, or monitoring equipment of the onset of drowsiness. The threshold of the timer circuitry 146 may be adjusted such that the CPU 140 detects relatively long periods of eye closure, as may occur when a person is falling asleep.

For example, because normal blinks are relatively short, the threshold may be set at a time ranging from close to zero seconds up to several seconds, preferably from about 200 milliseconds to about 300 milliseconds, and most preferably about 250 milliseconds, to distinguish normal blinks from drowsiness-induced eyelid movement. When the CPU 140 detects a drowsiness condition, i.e., detects a high light intensity signal exceeding the predetermined threshold time, it may activate a warning device. The warning device may be included within the processing box 130, such as the speaker 150, or alternatively on the frame, for example, by mounting a warning light (not shown) or an alarm speaker (not shown in FIG. 9, see FIG. 10C) on the frame.

Alternatively, the detection device 30 may be used to unobtrusively record or monitor drowsiness-induced eyelid movement, with the CPU 140 producing a stream of data 144 which the transmitter 152 may transmit to the receiving and processing unit 154 (FIG. 9). For example, the device 30 may be used in conjunction with a vehicle safety system to monitor a driver's level of awareness or attentiveness. The stream of data 144 may be transmitted to a receiving and processing unit 154 mounted in a vehicle, which may store data on the driver's drowsiness and/or may use the data to make decisions and control the vehicle, e.g., adjust the vehicle's speed or even turn the vehicle's engine off. Thus, the detection device 30 may be used to monitor truck drivers, taxi drivers, ship or airline pilots, train conductors or engineers, radar or airport control tower operators, operators of heavy equipment or factory machinery, scuba divers, students, astronauts, entertainment participants or observers, and the like. The signals may be stored and analyzed in real time for trend changes measured over time to predict drowsiness effects of individuals using the device.

The detection device 30 and system 14 may also be used in a medical diagnostic, therapeutic, research or professional setting to monitor the wakefulness, sleep patterns and/or the effects of drugs, which may affect blink rate, blink velocity, blink duration, or PERCLOS of a patient or vehicle operator. Similar to the method just described, the CPU 140 produces a stream of data 144, which the transmitter may send to a remote receiving and processing unit 154, which may store the stream of data 144 in the memory circuitry 160 for later retrieval and analysis by researchers, medical professionals, or safety personnel (e.g., similar to the way in which flight recorder data may be stored in an aircraft's "black box" recorder). The receiving and processing unit 154 may also display the stream of data 144, for example at a nurse's station, as an additional parameter to continually monitor a patient's physical, mental, or emotional condition. The unit 154 may store and/or produce a signal, e.g., by a series of algorithms, that must be responded to within a predetermined time (e.g., performance vigilance monitoring) to prevent false positives and negatives.

A number of medical conditions may be monitored by the detection device 30 and system 14, such as petit mal epilepsy, in which the eyes flutter at a rate of about three cycles per second, grand mal or psychometer seizures, where the eyes may stare or close repetitively in a jerky manner, myoclonic seizures, in which the lids may open and close in a jerky manner, or tics, or other eye movements, such as encountered by people with Tourette's syndrome. The system may be used to monitor g-lock of pilots caused by g-force effects, hypoxemia of passengers or crew in aircraft due to losses in cabin pressure, nitrogen narcosis or "the bends" in divers, or the effects of gases, chemicals, or biological agents on military personnel or other individuals.

The system may also be used to monitor psychological situations, for example, to detect when a person lies (e.g., by closing their eyes when lying), during hypnosis, to monitor attentiveness, the effects of medications, e.g., L-dopa and other anti-Parkinsonian medications or anti-convulsants, drugs, alcohol, toxins, or the effects of hypoxia or ventilation, and the like. Neurological conditions may also be monitored where the innervation or mechanical function of the eyelid may be affected, such as in Parkinson's disease, muscle diseases, e.g., myotonia, myotonic muscular dystrophy, blepharospasm, photophobia or light sensitivity, encephalopathy, seizures, Bell's palsy, or where the condition may produce eyelid drooping or ptosis, such as third cranial nerve palsy or paresis, brainstem lesions or stroke, tumors, infection, metabolic diseases, trauma, degenerative conditions, e.g., multiple sclerosis, amyotrophic lateral sclerosis, polyneuropathy, myesthenia gravis, botulism, tetanus, tetany, tardive dyskinesia, brainstem encephalitis, and other primary eyelid conditions, such as exophthalmos, thyrotoxicosis or other thyroid conditions.

Similarly, the detector device 30 may be used in biofeedback applications, for example, in biofeedback, hypnosis or psychological therapies of certain conditions (e.g. tic disorders). The detector device 30 may produce a stimulus, e.g. activating a light or speaker, and monitor the user's eyelid movement in anticipation of receiving a response, e.g., a specific sequence of blinks, acknowledging the stimulus within a predetermined time. If the user fails to respond, the processor may store the response, e.g. including response time, and/or may automatically transmit a signal, such as an alarm signal.

In addition, the detection device 30 may be used to monitor individuals in non-medical settings, such as during normal activity in a user's home or elsewhere. For example, individuals with involuntary medical conditions, such as epilepsy or narcolepsy, may be monitored, or other individuals, such as, infants and children, prison inmates, demented patients (e.g., with Alzheimer's disease), law enforcement personnel, military personnel, bank tellers, cashiers, casino workers, students, swing or graveyard shift workers, and the like, may be monitored. Similar application may be applied in a sleep laboratory for monitoring sleep patients to measure parameters, such as onset of sleep, sleep latency, time of eyelid closing or opening, time of awakening during the night, etc., or to animal research where eye blinking may be a factor to be studied. Similarly, the performance and vigilance abilities of the user may be tested and analyzed as a direct function of, or in relationship to, PERCLOS.

When the CPU 140 detects the presence of particular eyelid movement, such as an extensive period of eye closure which may occur, for example, during an epileptic seizure, a syncopal episode, a narcoleptic episode, or when dozing off while driving or working, the CPU 140 may produce an output signal which activates an alarm. Alternatively, the transmitter 152 may send an output signal to shut off equipment being used, to notify medical personnel, such as by automatically activating a telephone to dial emergency services, to signal remote sites, such as police stations, ambulances, vehicle control centers, guardians, and the like.

The system for communication 14 may also find useful application for voluntary communication. A user wearing the detection device 30 may intentionally blink in a predetermined pattern, for example, in Morse code or other blinked code, to communicate an understandable message to people or equipment (e.g., to announce an emergency). The CPU 140 may convert a light intensity signal 142 received from the sensor 33 and corresponding to the blinked code into a stream of data 144, or possibly directly into an understandable message including letters, words and/or commands.

The stream of data 144 may then be displayed on a video display 50 (see FIG. 1) coupled to the output port 148, or emitted as synthesized speech on the internal speaker 150. The stream of data 144 may be transmitted by the transmitter 152 via the signal 153 to the receiving and processing unit 154 for displaying messages, or for controlling equipment, such as household devices, connected to the control system 164. In addition to residential settings, the system 14 may be used by individuals in hospitalized or nursing care, for example by intubated, ventilated, restrained, paralyzed or weakened patients, to communicate to attending medical staff and/or to consciously signal a nurse's station. These include all patients who have no physical ability to communicate verbally, but who retain ability to communicate using eye blinking of one or both eyes (e.g., patients with amyotrophic lateral sclerosis, transverse myelitis, locked-in syndrome, cerebravascular strokes, terminal muscular dystrophy and those intubated on ventilation).

The device may be used in any environment or domain, e.g. through water or other substantially transparent fluids. Further, the device 30 may also be used as an emergency notification and/or discrete security tool. A person who may be capable of normal speech may wear the device 30 in the event of circumstances under which normal communication, i.e., speech, is not a viable option. For example, a bank or retail employee who is being robbed or is otherwise present during the commission of a crime may be able to discretely blink out a preprogrammed warning to notify security or to call law enforcement. Alternatively, a person with certain medical conditions may wear the device in the event that they are physically incapacitated, i.e., are unable to move to call for emergency medical care, but are still able to voluntarily move their eyes. In such cases, a pre-recorded message or identifying data (e.g. name of the user, their location, the nature of the emergency, etc.) may be transmitted to a remote location by a specific set of eyeblink codes or preprogrammed message. In this manner, the detection device 30 may be used to monitor patients in an ICU setting, patients on ventilators, prisoners, elderly or disabled persons, heavy equipment operators, truck drivers, motorists, ship and aircraft pilots, train engineers, radar or airport control tower operators, or as a nonverbal or subliminal tool for communication by military guards, police bank tellers, cashiers, taxi-drivers, and the like. The detection device 30 may also be used as a recreational device, for example, as a children's toy similar to a walkie-talkie or to operate a remote control toy vehicle.

In addition, it may be desirable to have the CPU 140 perform an additional threshold comparison to ensure continued use of the detection device 30. For example, additional timer circuitry may be coupled to the CPU 140 such that the CPU 140 may compare the light intensity signals received from the sensor 33 to a second predetermined threshold provided by the timer circuitry. Preferably, the second predetermined threshold corresponds to a time period during which a person would normally blink. If the CPU 140 fails to detect a normal blink within this time period or if the user fails to respond to a predetermined stimulus (e.g. a blinking light or sound), the CPU 140 may produce a signal, activating the speaker 150 or transmitting a warning using the transmitter 152.

This may be useful, if, for example, the detection device 30 is removed by a perpetrator during commission of a crime, falls off because of the onset of a medical episode, as well as to prevent "false alarms," or to measure the "state of attentiveness" of the user. Alternatively, performance vigilance tasks may be required of the user to determine whether the signal transmitted is a purposeful or "false alarm" signal, and also for measuring attention or drowsiness levels for purposes of biofeedback, and also to measure compliance of the user wearing the device.

Alternatively, the polarity of the output signal 142 may be reversed such that a stream of data is produced only when the eye is opened, for example, when monitoring patients in a sleep lab to measure onset of sleep, sleep latency, time of eyelid closure, etc., or to monitor sleeping prison inmates. For such uses, the CPU 140 may activate an alarm only when an open eye condition is detected, as will be appreciated by those skilled in the art.

Figure 8:
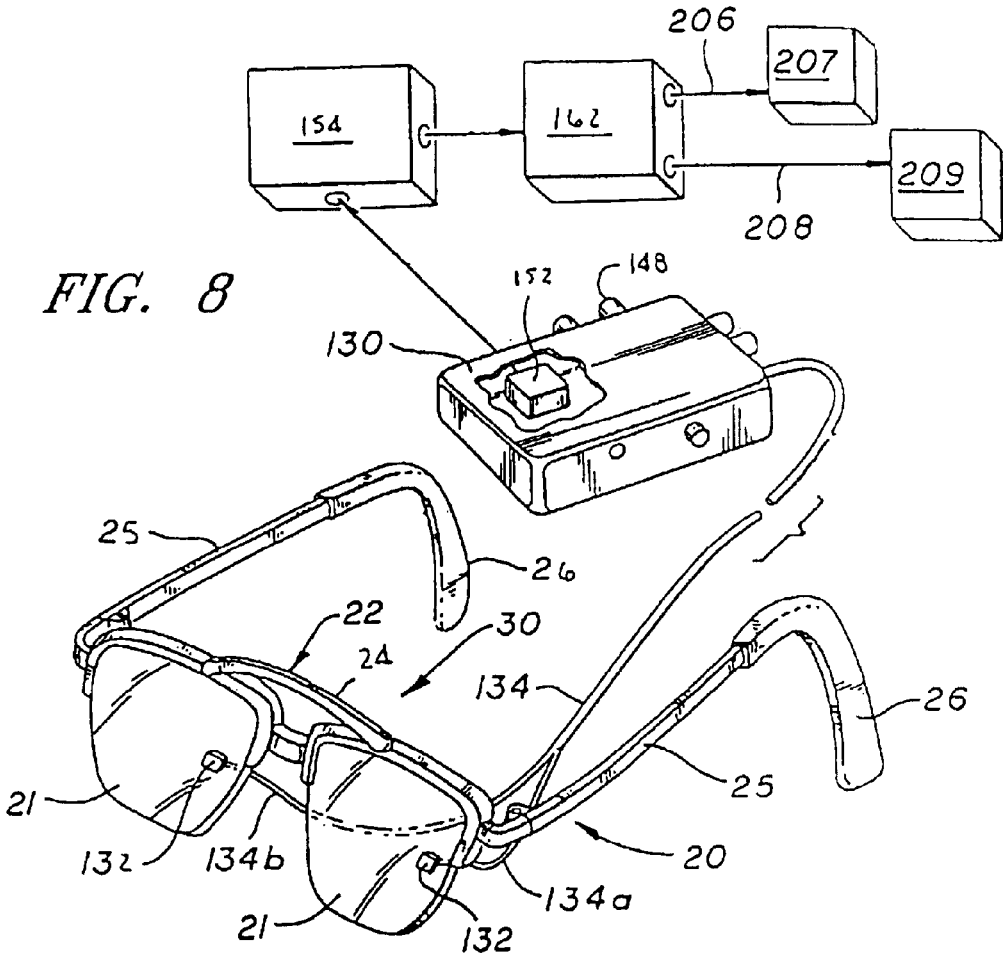
FIG. 8 is a perspective view and block diagram of another preferred embodiment of a system for communication using eyelid movement.

Turning to FIG. 8, another preferred embodiment of the detection device 30 in accordance with the present invention is shown. In this embodiment, the emitter and sensor are a single solid state light emission and detecting biosensor device 132 which are mounted directly onto the eyeglasses 20. The biosensor device 132, which preferably produces and detects infrared light, may be as small as 2 mm×4 mm and weigh only a few grams, thereby enhancing the convenience, comfort and/or discretion of the detection device 30. Because of the small size, the biosensor device 133 may be mounted directly in the lens 21, as shown in FIG. 8, on an outside or inside surface of the lens 21, in the bridgework 24 or at another location on the frame 22 that may facilitate detection of eye movement. The biosensor device 132 may measure less than about five millimeters by five millimeters surface area, and may weigh as little as about one ounce, thereby providing a emitter/sensor combination that may be unobtrusive to vision, portable, and may be conveniently incorporated into a light weight eye frame. Because the entire system may be self-contained on the frame, it moves with the user no matter which direction he or she looks and may operate in a variety of environments or domains, day or night, underwater, etc.

Hamamatsu manufactures a variety of infrared emitter and detector devices which may be used for the biosensor device 132, such as Model Nos. L1909, L1915-01, L2791-02, L2792-02, L2959, and 5482-11, or alternatively, a Radio Shack infrared emitter, Model No. 274-142, may be used. Multiple element arrays, e.g., linear optical scanning sensor arrays, appropriate for use with the present invention may be available from Texas Advanced Optoelectronic Solutions, Inc. (TAOS) of Plano, Tex., such as Model Nos. TSL 201 (64 pixels×1 pixel), TSL 202 (128×1), TSL 208 (512×1), TSL 2301 (102×1). These sensors may be used in combination with lens arrays to facilitate focusing of the detected light, such as the Selfoc lens array for line scanning applications made by NSG America, Inc. of Irvine, Calif.

In addition, multiple biosensor devices 132 may be provided on the eyeglasses 20, for example, a pair of biosensor devices 132 may be provided, as shown in FIG. 8, for detecting eyelid movement of each eye of the user (not shown). A cable 134 extends from each biosensor device 132 to a processing box 130, similar to the processing box 130 described above. The CPU 140 of the processing box 130 (not shown in FIG. 8) may receive and compare the output signal from each biosensor device 132 to further augment distinguishing normal blinks from other eyelid movement.

The pair of biosensor devices 132 may allow use of more sophisticated codes by the user, e.g., blinking each eye individually or together, for communicating more effectively or conveniently, as will be appreciated by those skilled in the art. In one form, a blink of one eye could correspond to a "dot," and the other eye to a "dash" to facilitate use of Morse code. The output signals from each eye could then be interpreted by the CPU 140 and converted into an understandable message.

In another form, a right eye blink (or series of blinks) may cause an electric wheelchair to move to the right, a left eye blink (or series of blinks) may move to the left, two simultaneous right and left eye blinks may cause the wheelchair to move forward, and/or four simultaneous right and left eye blinks may cause the wheelchair to move backward. Similar combinations or sequences of eye blinks may be used to control the on/off function, or volume or channel control of a television, AM/FM radio, VCR, tape recorder or other electronic or electromechanical device, any augmentative communications or controlling device, or any device operable by simple "on/off" switches (e.g., wireless television remote controls single switch television control units, universal remote controllers, single switch multi-appliance units with AC plug/wall outlet or wall switch modules, computer input adapters, lighted signaling buzzer or vibrating signal boxes, switch modules of all types, video game entertainment controller switch modules and switch-controlled electronic toys).

In additional alternatives, one or more lenses or filters may be provided for controlling the light emitted and/or detected by the biosensor device, an individual emitter and/or detector. For example, the angle of the light emitted may be changed with a prism or other lens, or the light may be columnated or focused through a slit to create a predetermined shaped beam of light directed at the eye or to receive the reflected light by the sensor. An array of lenses may be provided that are adjustable to control the shape, e.g. the width, etc., of the beam of light emitted or to adjust the sensitivity of the sensor. The lenses may be encased along with the emitter in plastic and the like, or provided as a separate attachment, as will be appreciated by those skilled in the art.

Figure 10A:
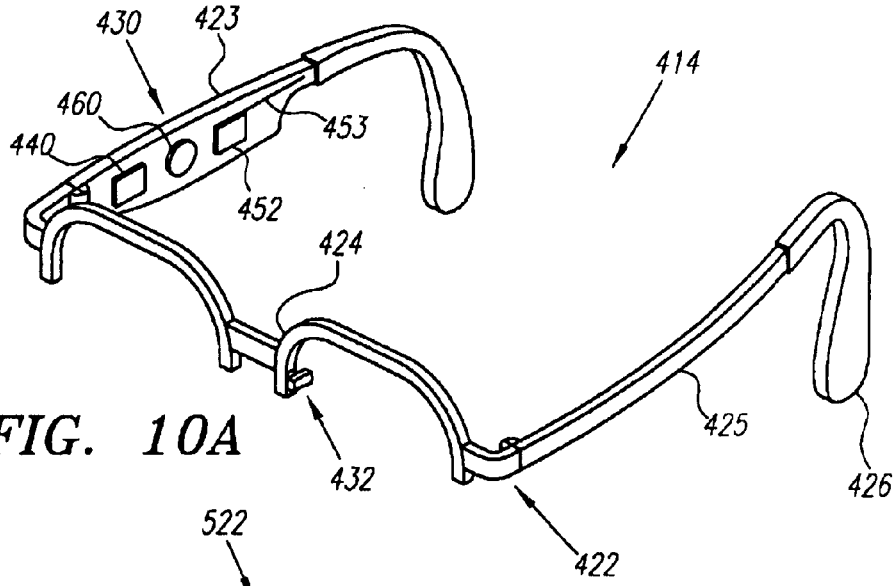
FIG. 10A is a perspective view of still another preferred embodiment of a system for communication using eyelid movement.

Turning now to FIG. 10A, another preferred embodiment of a system for communication 414 is shown, that includes a frame 422 including a biosensor device 432 with associated processor and transmitter circuitry 430 provided directly on the frame 422, for example, to enhance the convenience and discretion of the system for communication 414. The frame 422 may include a bridge piece 424 onto which the biosensor device 432 may be slidably and/or adjustably mounted, and a pair of ear supports 423, 425.

One of the supports 423 may have a larger size compared to the other support 425, for example, to receive the processor and transmitter circuitry 430 embedded or otherwise mounted thereon. A processor 440, similar to the CPU 140 in the processing box 130 previously described, may be provided on the frame 422, and a power source, such as a lithium battery 460, may be inserted or affixed to the support 423. A radio frequency or other transmitter 452 is provided on the support 423, including an antenna 453, which may be embedded or otherwise fastened along the ear support 423, in the temple piece or elsewhere in the frame 422.

The system 414 may also include manual controls (not shown) on the ear support 423 or elsewhere on the frame 422, for example to turn the power off and on, or to adjust the intensity and/or threshold of the biosensor device 432. Thus, a system for communication 414 may be provided that is substantially self-contained on the frame 422, which may or may not include lenses (not shown) similar to eyeglasses. External cables or wires may be eliminated, thereby providing a more convenient and comfortable system for communication.

Figure 10B:
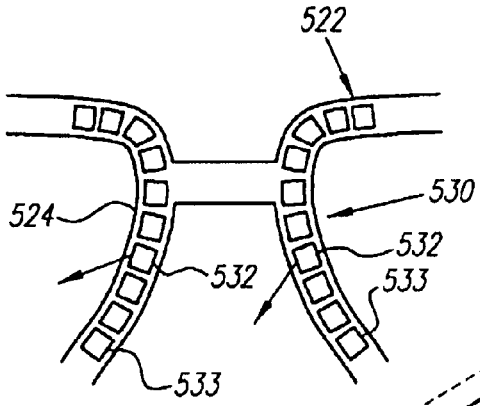
FIG. 10B is a schematic detail of a portion of the system of FIG. 10A.
Figure 10C:
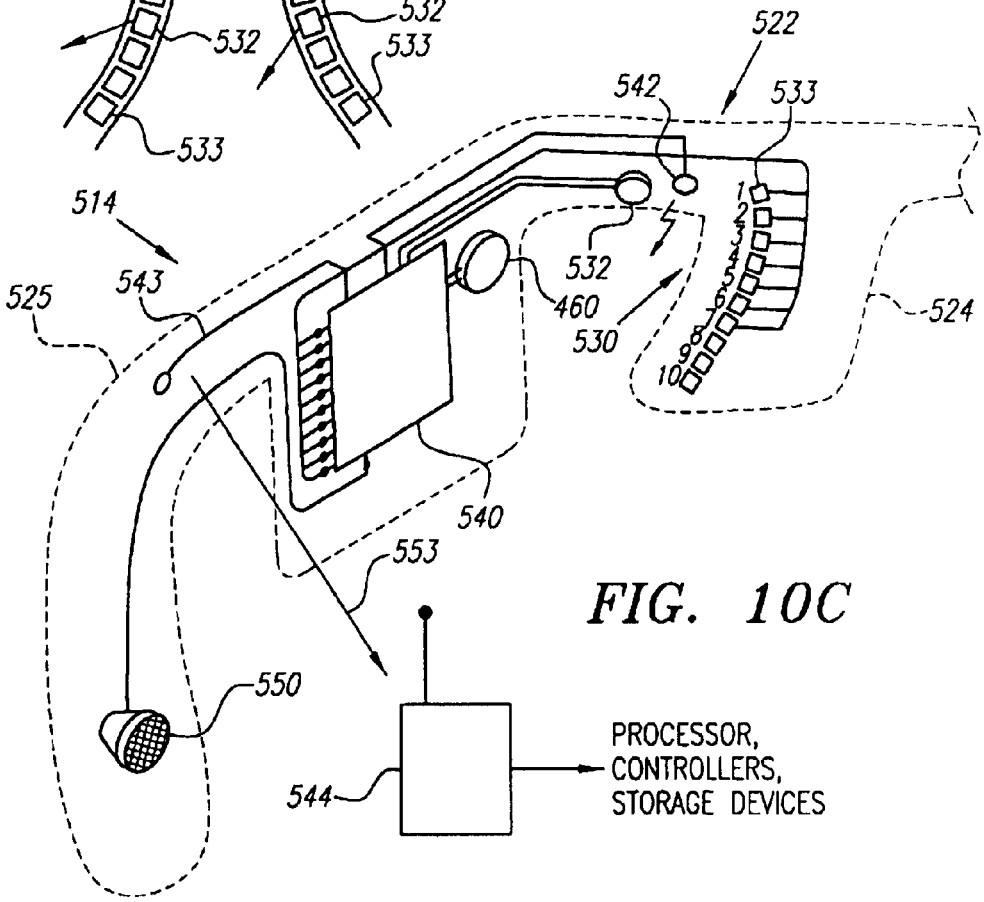
FIG. 10C is a detail of a preferred embodiment of an array of emitters and sensors that may be provided on a nose bridge of an eye frame, such as that of FIG. 10A.
Figure 10D:
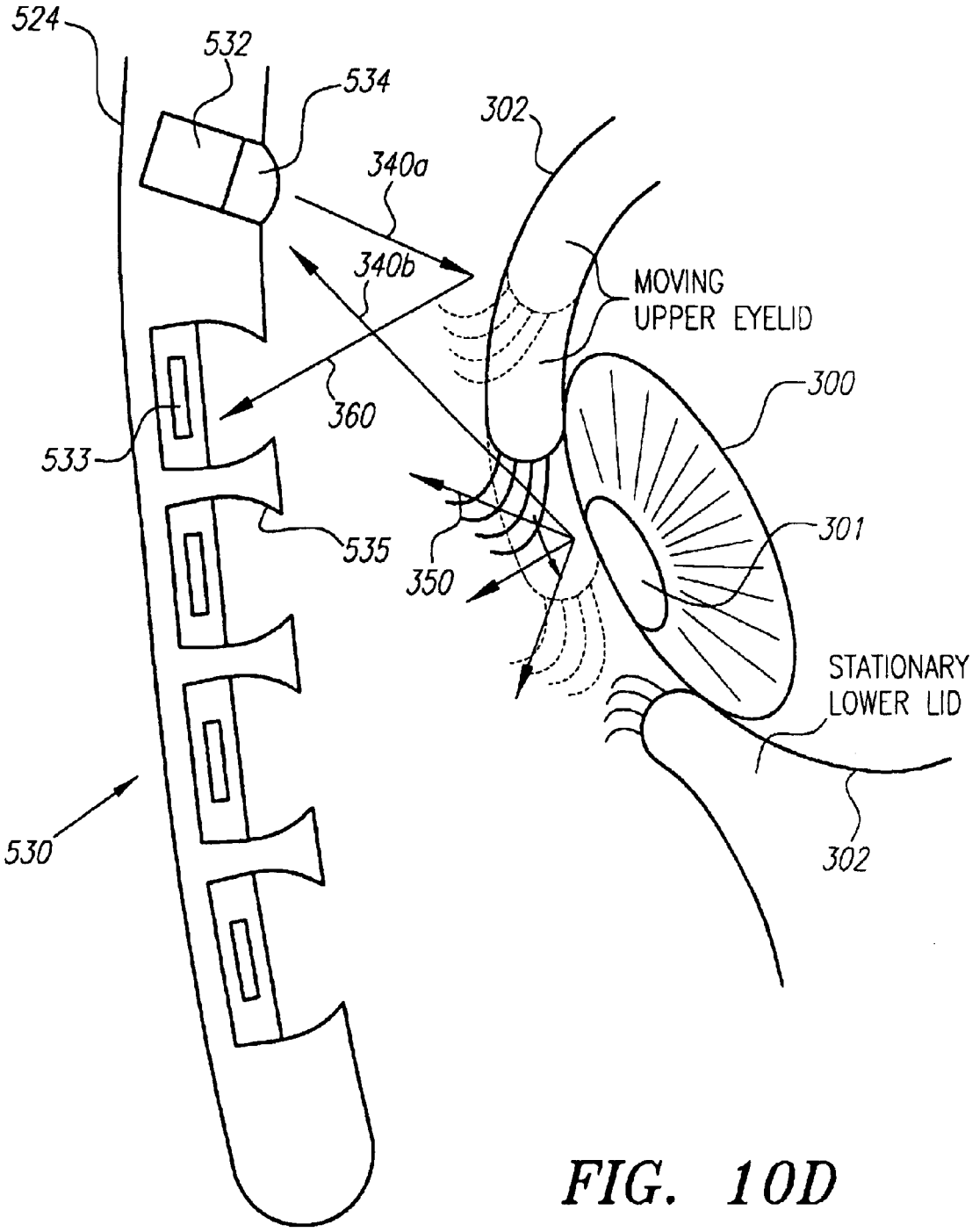
FIG. 10D is a sectional view of the array of emitters and sensors of FIG. 10C emitting light and detecting light reflected from an eye.

In another alternative, shown in FIGS. 10B, 10C, and 10D, a linear array 530 of emitters 532 and sensors 533 may be provided, preferably in a vertical arrangement mounted on a nose bridge 524 of an eye frame 522. A CPU 540, battery 460, transmitter antenna 543, and warning indicator 550 may also be provided on the frame 522, preferably in the temple piece 525, similar to the previously described embodiment. An LED 542 or similar stimulus device may also be provided at a predetermined location on the eye frame 522 to allow routine biofeedback responses from the user. In addition, a receiver 544 may be provided for receiving the stream of data created by the CPU 540 and transmitted by the transmitter 543.

As shown particularly in FIG. 10C, each of the sensors 533 and the emitter 532 are coupled to the CPU 540 or other control circuitry for controlling the emitter 532 and for processing the light intensity signals produced by the sensors 532. Thus, the CPU 540 may cycle through the sensors 533 in the array 530 and sequentially process the signal from each of the sensors 533, similar to the processors previously described. More preferably, as shown in FIG. 10D, the emitter 532 includes a lens 534 to focus a beam of light (indicated by individual rays 360a, 360b) onto the eye 300, preferably towards the pupil 301. The sensors 533 are embedded within the nose bridge 524 and a slit 535 is provided for each, the slits 535 having a predetermined size to control the reflected light detected by each sensor 533. Thus, each sensor 535 may detect movement of the eyelid 302 past a particular portion of the eye 300, e.g., to measure PERCLOS, as shown in FIG. 12A. The sensors or emitters may have lenses or columnating devices to focus emitted or reflected light.

The linear array 530 may facilitate measurement of additional parameters related to eyelid movement in addition to mere eye closure. For example, to measure the velocity of the eyelid opening or closing, i.e., the rate of eye closure, the CPU 540 may compare the time delay between the activation of successive sensors 533. In addition, the output signals from the sensors 553 may be processed to measure the percentage of pupil coverage of the eyelid 302, for example, due to partial eye closure, as a function of time, e.g., to monitor when the eye is partially, but not completely, closed, and/or to monitor the percentage of time that the eye is closed (PERCLOS), as shown in FIGS. 12A–12C, e.g., compared to the user's baseline of maximal eye opening.

Turning to FIG. 12D, in a further alternative, a two-dimensional array of sensors, such as a 5×5 array 633 or a 9×11 array, 733 may be provided. Other arrays including any number of elements in the array may be provided, and the invention should not be limited to the exemplary embodiments described herein. The sensors 633, 733 may then be used to measure surface area reflectivity of light from the emitter 632, i.e., the processor (not shown) may process the signals from each sensor in the array 633, 733 to create a stream of data indicating the percentage of surface area of the eye 300 covered by the eyelid 302.

The sensors in the array 633, 733 may be sufficiently sensitive or have sufficient resolution such that they may detect "red reflex" or the equivalent infrared "bright pupil" reflection due to the reflection of light off of the retina through the pupil 301. Thus, the sensors may produce a light intensity signal that includes a substantially zero value, indicating no red reflex or bright pupil, a low output, indicating red reflex or white pupil reflex, and a high output, indicating reflection off of a closed eyelid 302. The red reflex may appear as a bright white light pupil (resulting from infrared light from the emitter(s) reflecting off of the retina when the eyelid is open, or as a dark or "black pupil" if the processor uses subtraction algorithms, as is known in the art. The processor may thereby process the light intensity signals to detect when the pupil 301 is covered by the eyelid 302, i.e., at which point the user cannot see, even though their eye 300 may not be entirely covered by the eyelid 302, generally at a PERCLOS value of about 50–75 percent in primary gaze. Alternatively, as the eyelid, eye, and pupil descend, the sensor(s) may detect a red reflex or bright pupil even through the PERCLOS measurement may be as great as 75 –80 percent or more, e.g., where the eye may still see through a narrow slit-like palpebral fissure opening in downward gaze.

In another alternative, the processor and/or transmitter circuitry (such as the CPU 140 in the processor box 130 of FIG. 2, or the CPU's 440, 540 of FIGS. 10A and 10B) may include identification circuitry (not shown), either as a discrete memory chip or other circuit element, or within the CPU itself. The identification circuitry may be preprogrammed with a fixed identification code, or may be programmable, for example, to include selected identification information, such as the identity of the user, the user's location, an identification code for the individual detection device, and the like.

The CPU may selectively add the identification information to the transmitted stream of data 553, or the identification information may be automatically or periodically included in the stream of data 553, thereby allowing the stream of data 553 to be associated with a particular detection device, individual user and/or a specific location. The identification information may be used by the processor, for example, at a remote location, to distinguish between streams of data received from a number of detection devices, which may then be stored, displayed, etc. as previously described. Thus, the detection device may not require users to consciously communicate certain identification or other standard information when the system is used.

Figure 11A:
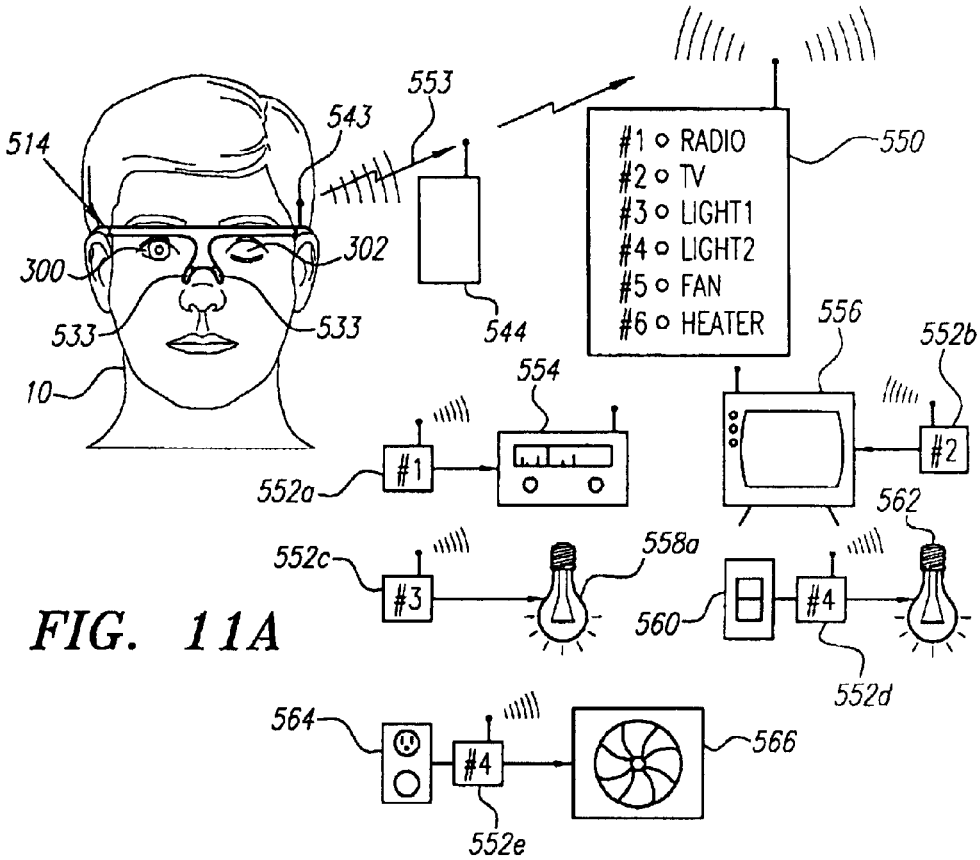
FIG. 11A is a schematic view of a system for selectively controlling a number of devices from a remote location based upon eyelid movement.

As shown in FIG. 11A, the receiver 544 may allow the user to control one or more devices coupled to the receiver 544 through a single switch multi-appliance control unit 550. The control unit 550 includes its own transmitter adapted to transmit on/off or other control signals that may be received by individual control modules 552a–552[f]*e*. The user 10 may blink to create a transmitted stream of data 553 that includes commands to turn off and on, or otherwise control, selected appliances using the control unit 550 and control modules 552a–552[f]*e*, such as, a radio 554, a television 556, a light 558a[.], a light 562 controlled by a wall switch 560, a fan 566 plugged into a wall socket 564, and the like.

Figure 11B:
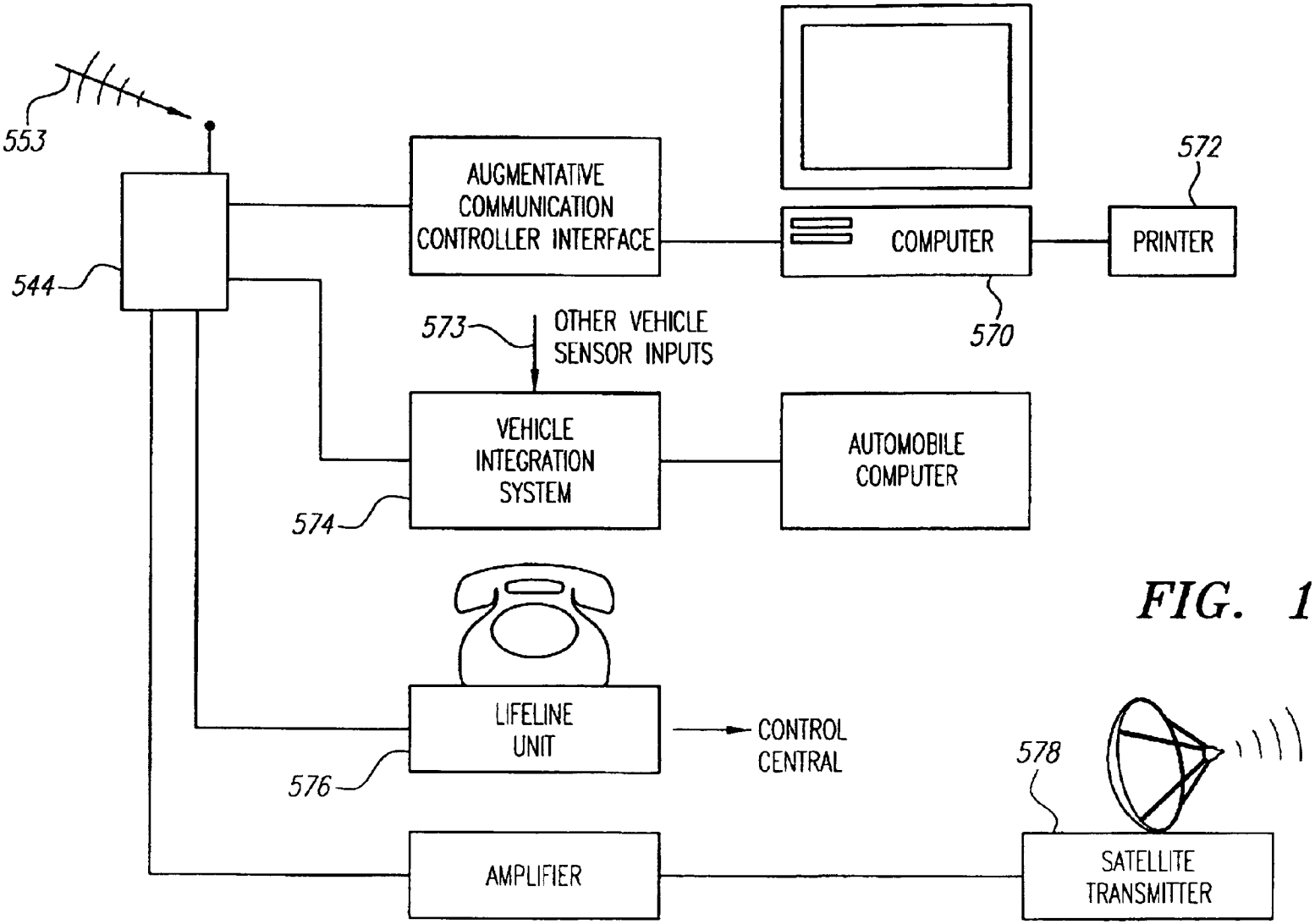
FIG. 11B is a schematic view of additional devices that may be controlled by the system of FIG. 11B.

Alternatively, as shown in FIG. 11B, the receiver 554 may be coupled to other systems, such as a computer 570 and printer 572, a vehicle integration system 574, a lifeline unit 576, a GPS or other satellite transmitter 578, and the like. The transmitted stream of data 553 may be processed alone or along with additional data, such as other vehicle sensor information 573, to further enhance monitoring a user, such as a long-distance truck driver.

Figures 13, 14:
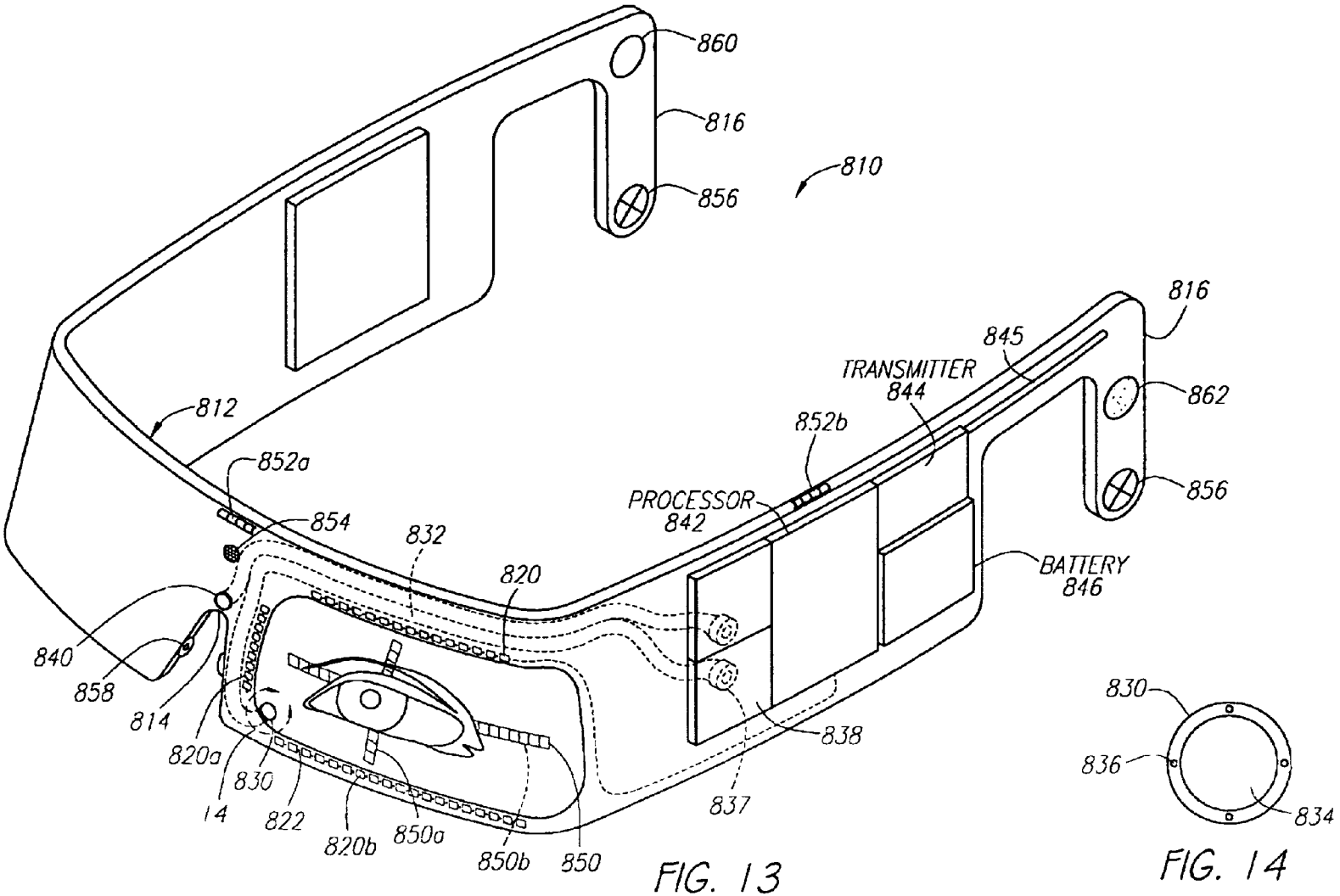
FIG. 13 is a perspective view of another system for monitoring eye movement, in accordance with the present invention.
FIG. 14 is a detail of a camera on the frame of FIG. 13.
Figures 15A, 15B, 15C, 15D, 15E:
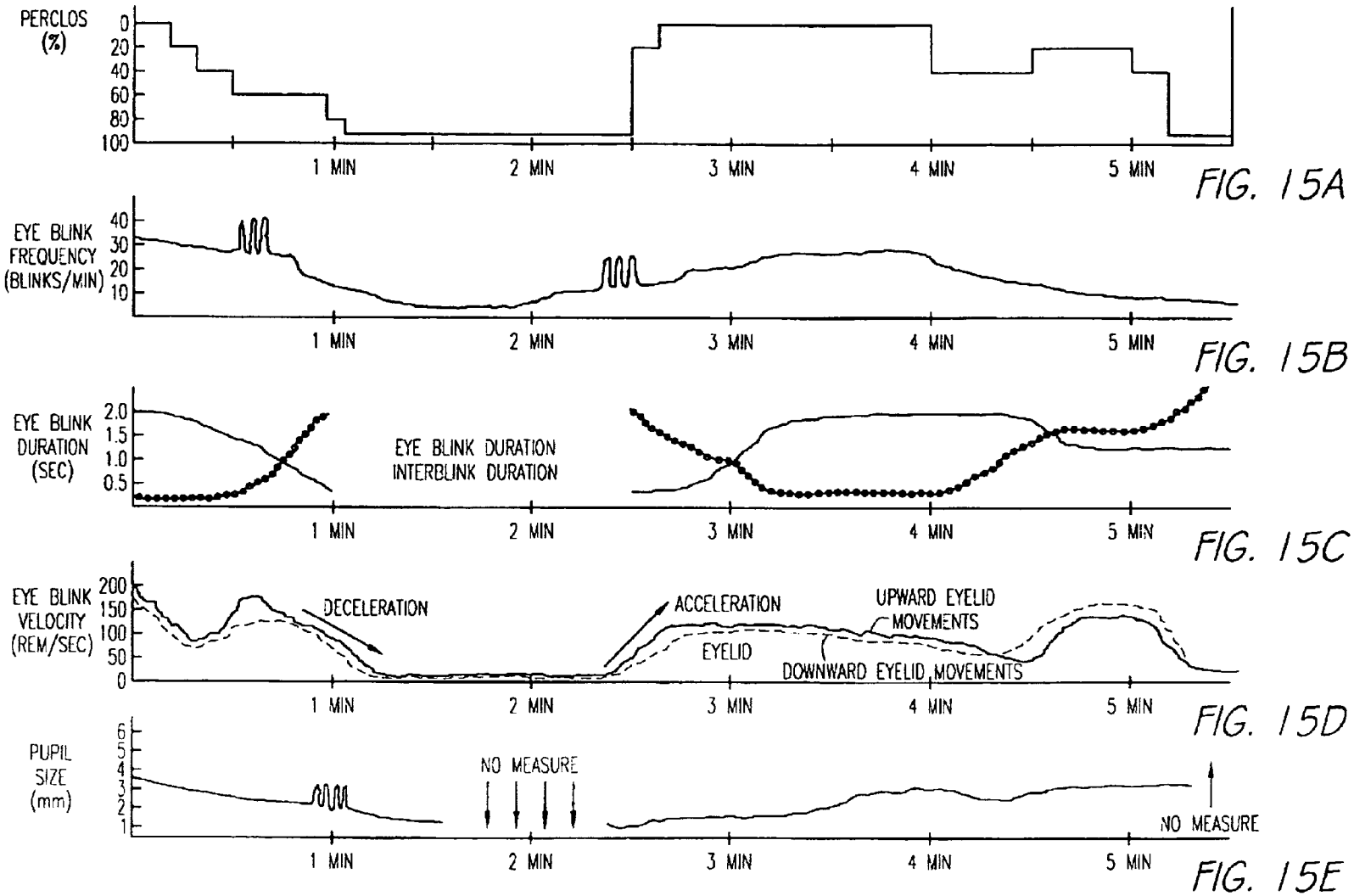
FIGS. 15A–15I are graphical displays of several parameters that may be monitored with the system of FIG. 13.
Figures 15F, 15G, 15H, 15I:
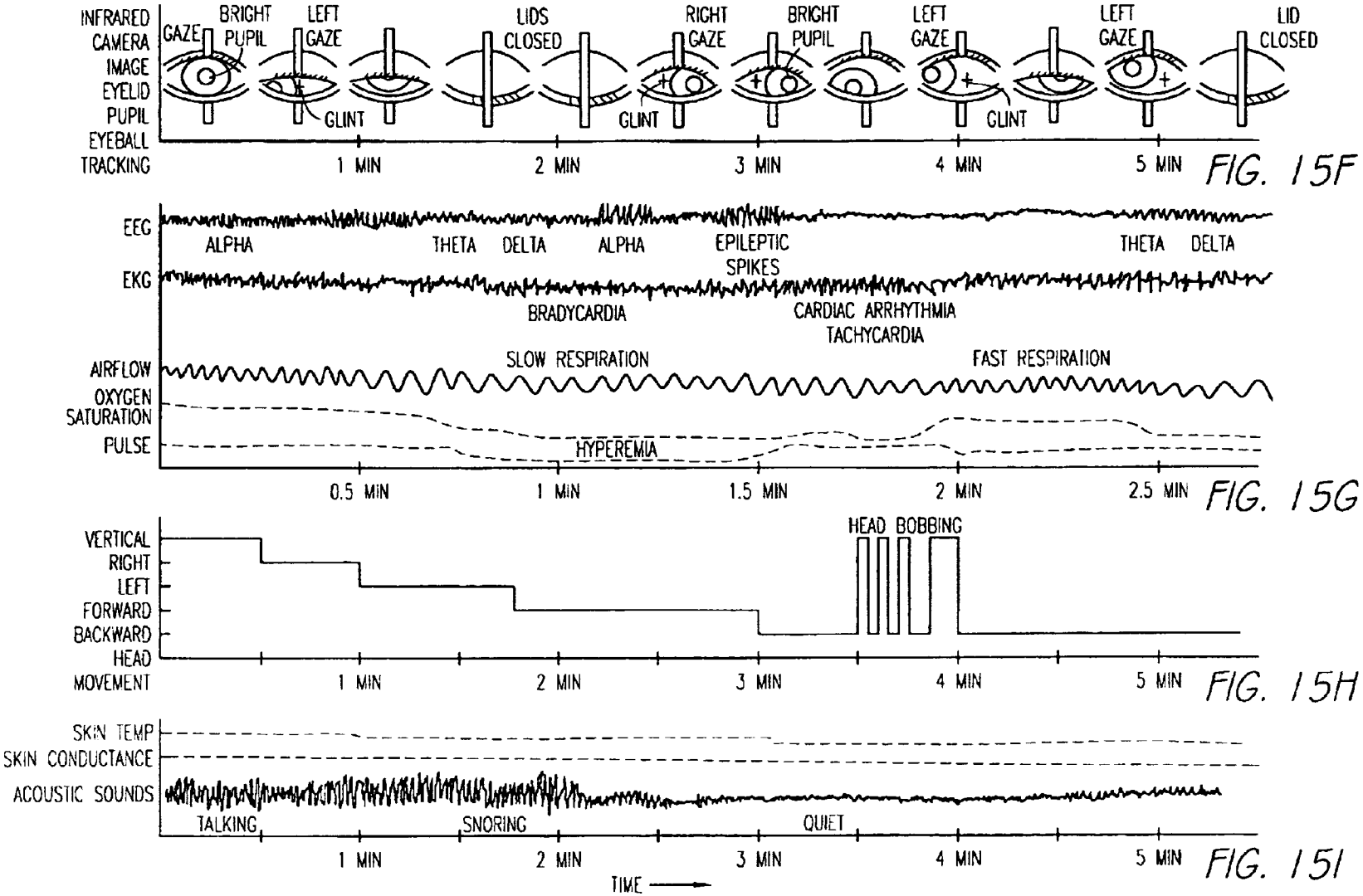

Turning to FIG. 13, yet another embodiment of a system 810 for monitoring eye movement is shown. Generally, the system 810 includes a frame 812 that may include a bridge piece 814 and a pair of car supports 816. The frame 812 may include a pair of lenses (not shown), such as prescription, shaded, or protective lenses, although they are not necessary for operation of the invention. Alternatively, the system may be provided on other devices that may be worn on a user's head, such as a pilot's oxygen mask, protective eye gear, a patient's ventilator, a scuba or swimming mask, a helmet, a hat, a head band, a head visor, and the like (not shown). The components of the system may be provided at a variety of locations on the device that generally minimize interference with the user's vision and/or normal use of the device.

An array of emitters 820 are provided on the frame 812, preferably in a vertical array 820a and a horizontal array 820b. In a preferred embodiment, the emitters 820 are infrared emitters configured to emit pulses at a predetermined frequency, similar to the embodiments described above. The emitters 820 are arranged on the frame such that they project a reference frame 850 onto the region of the user's eye. In a preferred embodiment, the reference frame includes a pair of crossed bands 850a, 850b dividing the region into four quadrants. The intersection of the crossed bands is preferably disposed at a location corresponding substantially to the eye's pupil during primary gaze, i.e., when the user is looking generally straight forward. Alternatively, other reference frames may be provided, generally including a vertical component and a horizontal component.

An array of sensors 822 are also provided on the frame 812 for detecting light from the emitters 820 that is reflected off of the user's eyelid. The sensors 822 preferably generate output signals having an intensity identifying whether the eyelid is closed or open, similar to the embodiments described above. Preferably, the sensors 822 are disposed adjacent to respective emitters 820 for detecting light reflected off of respective portions of the eyelid. Alternatively, sensors 822 may only be provided in a vertical array, e.g., along the bridge piece 814, for monitoring the amount of eyelid closure, similar to the embodiments described above. In a further alternative, the emitters 820 and sensors 822 may be solid state biosensors (not shown) that provide both the emitting and sensing functions in a single device.

Figure 17:
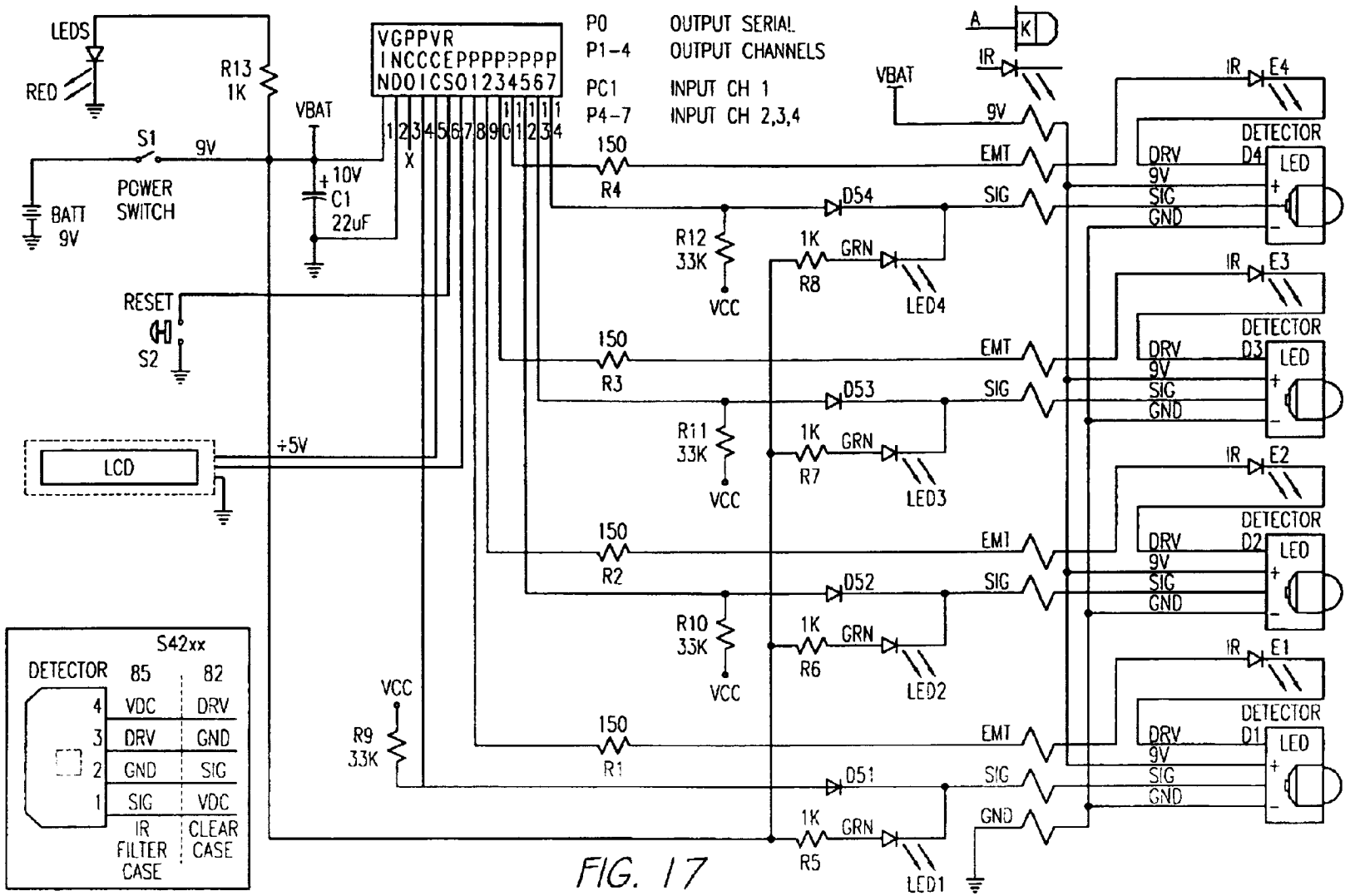
FIG. 17 is a schematic showing circuitry for processing signals from a five-element sensor array, in accordance with an exemplary embodiment of the present invention.

Circuitry may be provided for measuring PERCLOS or other parameters using the signals generated by the array of sensors. For example, FIG. 17 shows an exemplary schematic that may be used for processing signals from a five element array, e.g., to obtain PERCLOS measurements or other alertness parameters.

Returning to FIG. 13, the system 810 also includes a camera 830 provided on the frame [810] *812*. Preferably, the camera 830 is mounted on or adjacent the bridge piece 814 such that the camera 830 is oriented towards the region surrounding one of the user's eyes while minimizing interference with the user's vision. This camera 830 preferably includes a bundle of fiberoptic cables 832 that terminate in a lens 834, as shown in FIG. 14, on a first end mounted adjacent the bridge piece 814 and a second end 837 that is connected to a detector 838, e.g., a CCD or CMOS sensor, such as those used in endoscopes, that may convert an image into a digital video signal. The camera 830 is configured to detect the frequency of light emitted by the emitters 820, e.g., infrared light. The camera 830 may rely on the light projected by the emitters 820, or the fiberoptic cables 832 may include emitters 836 for projecting light, e.g., infrared light, onto the user's eyes and/or face. In addition, the system 810 may include a second camera 840 oriented away from the user's head, e.g., to monitor the user's surroundings.

One of the ear supports 816 may include a panel 818 for mounting a controller or other processor 842, a transmitter 844, an antenna 845, and a battery 846. Preferably, the processor [840] *842* is coupled to the emitters 820, the sensors 822, and/or the camera 830 for controlling their operation. The transmitter 844 may be coupled to the processor 842 for receiving the output signals from the sensors 822 and/or the video signals from the camera 830, e.g., to transmit the signals to a remote location, as described below. Alternatively, the transmitter 844 may be coupled directly to output leads from the sensors 822 and the camera 830. The frame 812 may also include manual controls (not shown), e.g., on the ear support 816, for example, to turn the power off and on, or to adjust the intensity and/or threshold of the emitters 820, the sensors 822, and/or the camera 830.

If desired, the system 810 may also include one or more additional sensors on the frame 812. The sensors may be coupled to the processor 842 and/or to the transmitter 844 so that the signals from the sensors may be monitored, recorded, and/or transmitted to a remote location. For example, one or more position sensors 852a, 852b may be provided, e.g., for determining the spatial orientation of the frame 812, and consequently the user's head. For example, actigraphic sensors may be provided to measure tilt or movement of the head, e.g., to monitor whether the user's head is drooping forward or tilting to the side. Acoustic sensors, e.g., a microphone 854 may be provided for detecting environmental noise or sounds produced by the user.

In addition or alternatively, the frame 812 may include one or more sensors for measuring one or more physical characteristics of the user. For example, EEG electrodes 856 may be provided on the ear support 816, above or below the nasion, and/or other region that may contact the patient's skin to measure brain activity, e.g., waking, drowsy, or other sleep-related brain activity. An EKG electrode (not shown) may be provided that is capable of measuring cardiac activity through a skin contact site. A pulse sensor (not shown) may be used to measure cardiovascular pulsations, or an oximetry sensor 858 may be used to measure oxygen saturation levels. A thermistor or other sensor may measure of respiratory air flow, e.g., through the user's nose. A thermistor, thermocouple, or other temperature sensor (not shown) may be provided for measuring the user's skin temperature. A sweat detector (not shown) may be provided for measuring moisture on the user's skin.

In addition, the system 810 may include one or more feedback devices on the frame 812. These devices may provide feedback to the user, e.g., to alert and/or wake the user, when a predetermined condition is detected, e.g., a state of drowsiness or lack of consciousness. The feedback devices may be coupled to the processor 842, which may control their activation. For example, a mechanical vibrator device 860 may be provided at a location that may contact the user, e.g., on the ear support 816, that may provide tactile vibrating stimuli through skin contact. An electrode (not shown) may be provided that may produce relatively low power electrical stimuli. A light emitter, such as one or more LED's may provided at desired locations, e.g., above the bridge piece 814. Alternatively, audio devices 862, such as a buzzer or other alarm, may be provided, similar to the previous embodiments. In a further alternative, aroma-emitters may be provided on the frame [810] *812*, e.g., on or adjacent in the bridge piece 814.

Alternatively, the feedback devices may be provided separate from the frame, but located in a manner capable of providing a feedback response to the user. For example, audio, visual, tactile (e.g., vibrating seat), or olfactory emitters may be provided in the proximity of the user, such as any of the devices described above. In a further alternative, heat or cold generating devices may be provided that are capable of producing thermal stimuli to the user, e.g., a remotely controlled fan or air conditioning unit.

The system 810 may also include components that are remote from the frame 812, similar to the embodiments described above. For example, the system 810 may include a receiver, a processor, and/or a display (not shown) at a remote location from the frame 812, e.g., in the same room, at a nearby monitoring station, or at a more distant location. The receiver may receive signals transmitted by the transmitter 842, including output signals from the sensors 822 or any of the other sensors provided on the frame 812 and/or the video signals from the camera 830.

A processor may be coupled to the receiver for analyzing signals from the components on the frame 812, e.g., to prepare the signals for graphical display. For example, the processor may prepare the video signals from the camera 830 for display on a monitor, thereby allowing personal monitoring of the user. Simultaneously, other parameters may be displayed, either on a single monitor or on separate displays. For example, [FIG. 15a] *FIGS. 15A-15I* shows signals indicating the output of various sensors that may be on the frame 812, which may be displayed along a common time axis or otherwise correlated, e.g., to movement of the user's eye and/or level of drowsiness. The processor may superimpose or otherwise simultaneously display the video signal in conjunction with the other sensed parameters to allow a physician or other individual to monitor and personally correlate these parameters to the user's behavior.

In a further alternative, the processor may automatically process the signals to monitor or study the user's behavior. For example, the processor may use the output signals to monitor various parameters related to eye movement, such as eye blink duration (EBD), eye blink frequency, eye blink velocity, eye blink acceleration, interblink duration (IBD), PERCLOS, PEROP (percentage eyelid is open), and the like.

Figure 16:
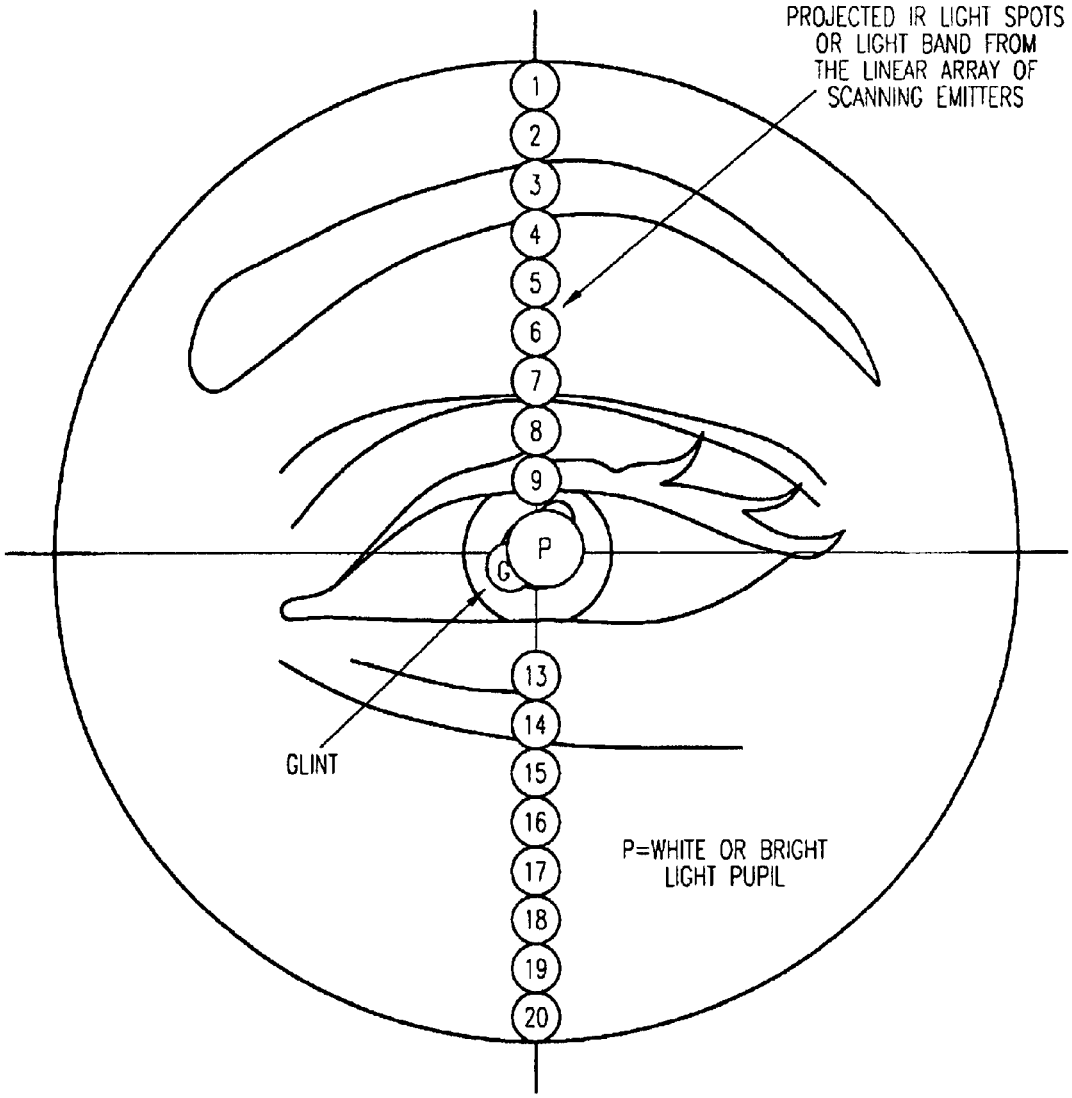
FIG. 16 is a detail of video output from a camera on the frame of FIG. 13.

The video signals from the camera 830 may be processed to monitor various eye parameters, such as pupillary size, location, e.g., within the four quadrant defined by the crossed bands 850, eye tracking movement, eye gaze distance, and the like. For example, because the camera 830 is capable of detecting the light emitted by the emitters 822, the camera 830 may detect a reference frame projected onto the region of the user's eye by the emitters. FIG. 16 shows an exemplary video output from a camera included in a system having twenty emitters disposed in a vertical arrangement. The camera may detect twenty discrete regions of light arranged as a vertical band. The camera may also detect a "glint" point, G, and/or a moving bright pupil, P. Thus, the movement of the pupil may be monitored in relation to the glint point, G, and/or in relation to the vertical band 1–20.

Because the emitters 822 are fixed to the frame 812, the reference frame 850 remains substantially stationary. Thus, the processor may determine the location of the pupil in terms of orthogonal coordinates (e.g., x-y or angle-radius) relative to the reference frame 850. Alternatively, if the reference frame is eliminated, the location of the pupil may be determined relative to any stationary "glint" point on the user's eye. For example, the camera 830 itself may project a point of light onto the eye that may be reflected and detected by the camera. This "glint" point remains substantially stationary since the camera 830 is fixed to the frame 812.

In addition, the video signals from a remote camera that may view the user's face from a distance may be used to monitor various facial measures, such as facial expression, yawning frequency, and the like, in addition to or [alternatively, the project] *instead of the projected* light reference frame from the emitters. In addition or alternatively, the parameters from other sensors may be processed and correlated, such as head orientation, tilt, body movement, physiological parameters, and the like. Preferably, the processor may correlate these parameters to generate a composite fatigue index (CFI) that is a function of two or more of these parameters. When a predetermined CFI is detected, the system 810 may activate an alarm or other notice to the user and/or to another party at a remote location. Thus, the system 810 may provide a more effective way to monitor the user's fatigue, drowsiness, alertness, mental state, and the like. In a further alternative, the system 810 may be used to generate predetermined outputs, e.g., to activate or deactivate equipment, such as a vehicle being operated by the user when a predetermined condition, e.g., CFI value, is determined by the system 810.

Alternatively, the processor may be provided on the frame 812, e.g. as part of processor 842, for monitoring the parameters for a predetermined event, such as a predetermined CFI value, to occur. Although only a single lens and set of emitters, sensors, and cameras are shown, it will be appreciated that another set may be provided for the other eye of the user of the system 810. In a further alternative, the eye tracking parameters described above may be monitored by a remote camera, e.g., in a fixed position in front of the user, such as the dashboard of a vehicle and the like. The remote camera may be coupled to the processor, either directly or via its own transmitter, as will be appreciated by those skilled in the art.

Thus, a system in accordance with the present invention may monitor or detect one or more parameters, such as those listed below in Table 1.

TABLE 1

| Potential Biometric Measures |
|---|
| EYELID MEASURES |
| Percentage of time (t) and the amount palpebral fissure is opened (PEROP-t, -d, -dt), or closed (PERCLOS-t, -d, -dt), |
| lid droop |
| Eye Blink Duration (EBD) |
| Eye Blink Frequency (EBF) |
| Eye Blink Velocity (EBV) |
| Eye Blink Accelaration (EBAc) |
| Deceleration (EBDc) |
| Interblink duration (IBD) |
| Eye blink flurries |
| PUPIL MEASURES |
| Pupillary Appearance or Disappearance (with eyelid movement) |
| Pupillary Size Measurement (PSM) |
| Presence and quality of Pupillary |
| Dilation or Construction |
| (including Hippus) |
| EYEGLAZE MEASURES |
| Eye Tracking Movements (ETM) |
| including Directional Nystagmus |
| Eye Gaze Distance (EGD) and Direction |
| Eye Movement Distance |
| Eye Movement Velocity (EMV) |
| Eye Movement Acceleration (EMA) |
| and Deceleration (EMD) |
| Eye Movement Frequency (EMF) |
| Phoria/eye Drill Measures (PDM) |
| HEAD ORIENTATION MEASURES |
| Head Direction or Orientation (HDir) |
| HEAD MOVEMENT MEASURES |
| Head Nodding Frequency (HNF) |
| Head Tilt (HT) |
| OTHER NON-VIDEO SENSOR METRICS |
| EEG, EKG, pulse, oxygen saturation, respiration rate, body temp, skin conductance, actigraphic movements, head tilt sensors |

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A system for monitoring movement of a person's eye, comprising:

a device configured to be worn on a person's head;

[an array of] *one or more* emitters on the device for directing light towards an eye of the person when the device is worn[, the array of emitters configured for projecting a reference frame towards the eye]; [and]

a camera [oriented towards the eye for monitoring movement of the eye relative to the reference frame] *mounted on the device*; and one or more sensors on the device for detecting light from the [array of] *one or more* emitters that is reflected off of the eye or its eyelid, the one or more sensors producing an output signal indicating when the eye is open or closed.

2. The system of claim 1, wherein the one or more sensors comprise an array of sensors in a predetermined relationship with the [array of] *one or more* emitters for detecting light from the [array of] *one or more* emitters that is reflected off of respective portions of the eye or its eyelid, each sensor producing an output signal indicating when the respective portion of the eye is covered or not covered by the eyelid.

3. The system of claim 1, wherein the [array of] *one or more* emitters and the one or more sensors are disposed separately and substantially laterally from one another.

4. The system of claim 1, wherein the [array of] *one or more* emitters and the one or more sensors comprise solid state devices capable of operating both as an emitter and as a sensor.

5. The system of claim 1, wherein the camera is configured for producing a video signal, and wherein the system further comprises a processor for correlating the output signal from the one or more sensors with the video signal from the camera for determining the person's level of drowsiness.

6. The system of claim 5, further comprising a warning indicator on the device, the warning indicator being activated when the processor determines a predetermined level of drowsiness has occurred.

7. The system of claim 1, wherein the [array of] *one or more* emitters comprises a plurality of emitters disposed in a substantially vertical arrangement on the device.

8. The system of claim 7, wherein the [array of] *one or more* emitters further comprises a plurality of emitters disposed in a substantially horizontal arrangement on the device.

9. The system of claim 1, wherein the [array of] *one or more* emitters [is] *comprise an array of emitters* configured for projecting a set of crossed bands towards the eye for dividing a region including the eye into four quadrants.

10. The system of claim 1, further comprising a transmitter on the device for wireless transmission of video output signals from the camera to a remote location.

11. The system of claim 1, wherein the [array of] *one or more* emitters comprise infrared emitters configured to emit pulses of infrared light.

12. The system of claim 11, wherein the camera comprises an infrared camera.

[13. The system of claim 1, wherein the camera is mounted on the device.]

14. The system of claim [13]*1*, wherein the camera comprises a fiberoptic assembly.

15. The system of claim [13]*1*, wherein the camera comprises at least one of a CCD and CMOS detector.

16. The system of claim 1, further comprising a sensor on the device for detecting one or more physiological characteristics of the person.

17. The system of claim 16, wherein the sensor comprises at least one of a EEG electrode, an EKG electrode, an oximetry sensor, a pulse sensor, an airflow sensor, and a temperature sensor.

18. The system of claim 1, further comprising at least one of an orientation sensor for detecting the spatial orientation of the device and an actigraphic sensor.

19. The system of claim 1, wherein the device comprises at least one of an eyeglass frame, a hat, a helmet, a visor, and a mask.

20. A system for monitoring movement of a person's eye, comprising:

a frame configured to be worn on a person's head;

an array of emitters on the frame for directing light towards an eye of the person when the device is worn, the array emitters configured to project a reference frame towards the eye;

an array of sensors on the frame in a predetermined relationship with the array of emitters for detecting light from the array of emitters that is reflected off of respective portions of the eye or its eyelid, each sensor producing an output signal indicating when the respective portion of the eye is covered or not covered by the eyelid; *and* a camera on the frame for monitoring movement of the eye relative to the reference frame, the camera configured for producing a video signal of a region of the eye and the reference frame[; and]

[a transmitter coupled to the sensor for wireless transmission of the output signal and the video signal to a remote location].

21. The system of claim 20, further comprising a processor for correlating the output signal and the video signal to determine the person's level of drowsiness.

22. The system of claim 21, further comprising a display for providing a graphical output of the output signal simultaneous with the video signal.

[23. A method for monitoring movement of a person's eye using a detection device including an array of emitters that are directed towards an eye of the person when the detection device is worn, and a camera oriented towards the eye, the method comprising:

emitting light from the array of emitters towards the eye to project a reference frame onto the eye;

monitoring movement of the eye relative to the reference frame with the camera; and generating a graphical output of the movement monitored by the camera relative to the reference frame;

wherein the detection device further comprises one or more sensors, and wherein the method further comprises detecting light from the array of emitters reflected off of the eye with the one or more sensors, the one or more sensors producing a light intensity signal indicating when the eye is open or closed.]

[24. The method of claim 23, wherein the array of sensors is disposed in a predetermined relationship with the array of emitters for detecting light from the array of emitters that is reflected off of respective portions of the eye or its eyelid, each sensor producing an output signal indicating when the respective portion of the eye is covered or not covered by the eyelid.]

[25. The method of claim 24, further comprising correlating the output signal from the one or more sensors with video signals produced by the camera monitoring movement of the eye relative to the reference frame, thereby determining the person's level of alertness.]

[26. The method of claim 23, wherein the monitoring step comprises measuring movement of the eye's pupil relative to the reference frame.]

[27. The method of claim 26, further comprising graphically displaying the movement of the eye's pupil relative to the reference frame.]

[28. The method of claim 25, further comprising providing a warning to the person when the determined level of alertness falls below a predetermined level.]

*29. The system of claim 1, wherein the camera is oriented towards the eye for monitoring movement of the eye.*

*30. The system of claim 1, wherein the camera is oriented away from the person to monitor the person's surroundings.*

*31. A system for monitoring movement of a person's eye, comprising:*

*a device configured to be worn on a person's head;*

*one or more emitters on the device for directing light towards an eye of the person when the device is worn;*

*an imaging sensor on the device comprising a lens directed towards the eye of the person when the device is worn, the sensor configured for converting images of the eye into output signals;*

*a processor coupled to the sensor for monitoring one or more eye movement parameters of the eye based upon the output signals; and*

*one or more physiological sensors on the device for monitoring one or more physiological parameters.*

*32. The system of claim 31, further comprising a display coupled to the imaging sensor and the one or more physiological sensors for displaying the one or more eye movement parameters of the eye and the one or more physiological parameters.*

*33. The system of claim 31, wherein the imaging sensor further comprises a bundle of fiberoptic cables comprising a first end terminating in the lens.*

*34. A system for monitoring movement of a person's eye, comprising:*

*a device configured to be worn on a person's head;*

*one or more emitters on the device for directing light towards an eye of the person when the device is worn;*

*a two-dimensional array of sensors on the device directed towards the eye of the person when the device is worn, the sensors configured for converting images of the eye into output signals;*

*a processor coupled to the sensors for monitoring one or more eye movement parameters of the eye based upon the output signals; and*

*one or more sensors on the device for detecting one or more physiological characteristics of the person, the processor further configured for correlating the one or more physiological characteristics with the output signals to generate a composite fatigue index of the person wearing the device.*

*35. The system of claim 34, further comprising a camera on the device that is oriented away from the person to monitor the person's surroundings.*

*36. A system for monitoring movement of a person's eye, comprising:*

*a device configured to be worn on a person's head;*

*one or more emitters on the device for directing light towards an eye of the person when the device is worn;*

*one or more sensors on the device for detecting light from the one or more emitters that is reflected off of the eye or its eyelid, the sensors configured for converting images of the eye into output signals;*

*one or more position sensors for determining a spatial orientation of the device when the device is worn; and*

*a processor coupled to the one or more sensors for monitoring one or more eye movement parameters of the eye based upon the output signals and coupled to the one or more position sensors, the processor correlating at least the spatial orientation determined using the one or more position sensors with the output signals to generate a composite fatigue index of the person wearing the device.*

*37. The system of claim 36, wherein the one or more position sensors comprise one or more actigraphic sensors to measure tilt or movement of the person's head when the device is worn.*

*38. A method for monitoring movement of a person's eye using a detection device including one or more emitters and an array of sensors that are directed towards an eye of the person when the detection device is worn, the method comprising:*

*emitting light from one or more emitters towards the eye;*

*detecting light from the one or more emitters reflected off of the eye with the array of sensors, the array of sensors producing light intensity signals indicating when the eye is open or closed; and*

*monitoring one or more eye movement parameters of the eye based upon the light intensity signals,*

*wherein the one or more eye movement parameters are monitored to monitor a psychological condition of the person.*

*39. The method of claim 38, wherein the one or more eye movement parameters are monitored to detect whether the person is lying.*

*40. A method for monitoring movement of a person's eye using a detection device including one or more emitters and an array of sensors that are directed towards an eye of the person when the detection device is worn, the method comprising:*

*emitting light from one or more emitters towards the eye;*

*detecting light from the one or more emitters reflected off of the eye with the array of sensors, the array of sensors producing light intensity signals indicating when the eye is open or closed; and*

*monitoring one or more eye movement parameters of the eye based upon the light intensity signals,*

*wherein the one or more eye movement parameters are monitored to monitor a medical condition of the person.*

*41. The method of claim 40, wherein the one or more eye movement parameters are monitored to monitor a neurological condition of the person.*

*42. A method for monitoring movement of a person's eye using a detection device including one or more emitters and an array of sensors that are directed towards an eye of the person when the detection device is worn, the method comprising:*

*emitting light from one or more emitters towards the eye;*

*detecting light from the one or more emitters reflected off of the eye with the array of sensors, the array of sensors producing light intensity signals indicating when the eye is open or closed; and*

*monitoring one or more eye movement parameters of the eye based upon the light intensity signals,*

*wherein the one or more eye movement parameters are monitored to monitor biofeedback from the person.*

*43. A method for monitoring movement of a person's eye using a detection device including one or more emitters and an array of sensors that are directed towards an eye of the person when the detection device is worn, the method comprising:*

*emitting light from one or more emitters towards the eye;*

*detecting light from the one or more emitters reflected off of the eye with the array of sensors, the array of sensors producing light intensity signals indicating when the eye is open or closed; and*

*transmitting data signals to communicate with a remote location, the data signals comprising the light intensity signals and identification information transmitted with the light intensity signals to distinguish the detection device from a number of detection devices.*

*44. The method of claim 43, further comprising monitoring the person from the remote location using the light intensity signals.*

*45. The method of claim 44, further comprising activating or deactivating equipment when a predetermined condition is detected using the light intensity signals.*

*46. A method for monitoring movement of a person's eye using a detection device including one or more emitters and an array of sensors that are directed towards an eye of the person when the detection device is worn, the method comprising:*

*emitting light from one or more emitters towards the eye;*

*detecting light from the one or more emitters reflected off of the eye with the array of sensors, the array of sensors producing light intensity signals indicating when the eye is open or closed; and*

*transmitting the light intensity signals to communicate with a remote location;*

*monitoring the person from the remote location using the light intensity signals; and*

*activating a warning indicator when a predetermined condition is detected using the light intensity signals.*

* * * * *